US011376294B2

(12) United States Patent
Jimenez del Rio et al.

(10) Patent No.: US 11,376,294 B2
(45) Date of Patent: Jul. 5, 2022

(54) MANGIFERIN-CONTAINING COMPOSITIONS FOR IMPROVING SPORTS PERFORMANCE

(71) Applicant: Polifenoles Naturales, S.L., Las Palmas (ES)

(72) Inventors: Miguel Jimenez del Rio, Telde (ES); Julia C. Wiebe, Las Palmas de GC (ES); Laura Lopez-Rios, Las Palmas de GC (ES); Tanausu Vega-Morales, Las Palmas de GC (ES); Ruben Perez-Machin, Las Palmas de GC (ES); Alvaro Sanchez-Rodriquez, Las Palmas de GC (ES); Carlos J. Mateos, Las Palmas de GC (ES); Nigel Peter Gericke, Cape Town (ZA)

(73) Assignee: NEKTIUM PHARMA S.L., Las Palmas (ES)

( * ) Notice: Subject to any disclaimer, the term of this patent is extended or adjusted under 35 U.S.C. 154(b) by 245 days.

(21) Appl. No.: 16/365,015

(22) Filed: Mar. 26, 2019

(65) Prior Publication Data

US 2019/0216872 A1    Jul. 18, 2019

Related U.S. Application Data

(63) Continuation-in-part of application No. 15/214,263, filed on Jul. 19, 2016, now Pat. No. 10,537,604.

(51) Int. Cl.
| | | |
|---|---|---|
| *A61K 36/22* | (2006.01) | |
| *A61K 36/48* | (2006.01) | |
| *A61K 36/51* | (2006.01) | |
| *A61K 36/38* | (2006.01) | |
| *A61K 36/725* | (2006.01) | |
| *A61K 31/522* | (2006.01) | |
| *A61K 36/69* | (2006.01) | |
| *A61K 31/352* | (2006.01) | |
| *A61K 31/7048* | (2006.01) | |
| *A61P 25/00* | (2006.01) | |
| *A61K 36/8905* | (2006.01) | |
| *A61K 45/06* | (2006.01) | |
| *A61K 36/37* | (2006.01) | |
| *A61K 9/48* | (2006.01) | |
| *A61K 9/68* | (2006.01) | |
| *A61K 9/00* | (2006.01) | |
| *A61K 9/46* | (2006.01) | |

(52) U.S. Cl.
CPC ............ *A61K 36/22* (2013.01); *A61K 31/352* (2013.01); *A61K 31/522* (2013.01); *A61K 31/7048* (2013.01); *A61K 36/37* (2013.01); *A61K 36/38* (2013.01); *A61K 36/48* (2013.01); *A61K 36/51* (2013.01); *A61K 36/69* (2013.01); *A61K 36/725* (2013.01); *A61K 36/8905* (2013.01); *A61K 45/06* (2013.01); *A61P 25/00* (2018.01); *A61K 9/006* (2013.01); *A61K 9/0007* (2013.01); *A61K 9/0058* (2013.01); *A61K 9/48* (2013.01)

(58) Field of Classification Search
CPC ... A61K 31/7048; A61K 31/352; A61K 36/38
See application file for complete search history.

(56) References Cited

U.S. PATENT DOCUMENTS

| | | |
|---|---|---|
| 4,436,732 A | 3/1984 | Vichkanova |
| 4,518,592 A | 5/1985 | Rusakova |
| 5,900,267 A | 5/1999 | Monros |
| 6,277,850 B1 | 8/2001 | Lubisch |
| 6,613,797 B2 | 9/2003 | Winter |
| 7,854,948 B2 | 12/2010 | Slimak |
| 8,277,850 B2 | 10/2012 | Paufique |
| 8,334,267 B2 | 12/2012 | Teng |
| 8,481,500 B2 | 7/2013 | Almau |
| 9,163,312 B2 | 10/2015 | Woods |
| 10,537,604 B2 | 1/2020 | Del Rio |
| 10,874,708 B2 | 12/2020 | Jiménez del Rio et al. |
| 2011/0046077 A1 | 2/2011 | Talamond et al. |
| 2013/0115329 A1* | 5/2013 | Savant ................... A23L 29/30 426/2 |
| 2014/0220220 A1 | 8/2014 | Arday et al. |
| 2015/0056299 A1 | 2/2015 | Randall |

FOREIGN PATENT DOCUMENTS

| | | |
|---|---|---|
| CN | 101003558 A | 7/2007 |
| CN | 101269161 A | 9/2008 |
| CN | 101270230 A | 9/2008 |
| CN | 101731710 A | 6/2010 |
| CN | 101732360 A | 6/2010 |

(Continued)

OTHER PUBLICATIONS

T E Graham Review Sports Med. 2001;31(11)785-807. Abstract only. (Year: 2001).*
Non-Final Office Action dated Jun. 19, 2020 in corresponding U.S. Appl. No. 16/318,457.
Ding, et al., "Norathyriol reverses obesity—and high-fat-diet-induced insulin resistance in mice through inhibition of PTP1B", Diabetologia, 57, pp. 2145-2154. (2014).
Non-Final Office Action dated Aug. 26, 2020 in corresponding U.S. Appl. No. 16/318,457.

(Continued)

*Primary Examiner* — Amy L Clark
(74) *Attorney, Agent, or Firm* — Kramer & Amado, P.C.

(57) ABSTRACT

A method for enhancing at least one of alertness, attention, concentration and memory in a person in need thereof, comprising co-administering an effective amount of mangiferin, norathyriol, or an extract comprising mangiferin or norathyriol; and caffeine to the person. The components may be co-administered in a single composition, or administered in separate compositions. The mangiferin and/or norathyriol exhibit synergistic effects on brain wave activity when co-administered with caffeine.

19 Claims, 10 Drawing Sheets

(56) References Cited

FOREIGN PATENT DOCUMENTS

| CN | 101848922 A | 9/2010 |
|---|---|---|
| CN | 102920696 A | 2/2013 |
| CN | 103191141 A | 7/2013 |
| CN | 104557892 A | 4/2015 |
| EP | 2 444 094 A1 | 4/2012 |
| RU | 2176516 C1 | 12/2001 |
| RU | 2197259 C1 | 1/2003 |
| WO | 2008/061480 A1 | 5/2008 |
| WO | 2017/203540 A1 | 12/2017 |

OTHER PUBLICATIONS

Bolz, "Coffee and Caffeine: How Caffeine makes you feel more awake", Internet posting date Jan. 1, 2010, 5 pages. (Retrieved from https://indianapublicmedia.org/amomentofscience/coffee-caffeine on Nov. 19, 2018).
Smith, et al., "Breakfast Cereal and Caffeinated Coffee: Effects on Working Memory, Attention, Mood and Cardiovascular Function", Physiology & Behavior, vol. 37, Issue 1, pp. 9-17. (Aug. 1, 1999).
E. Eteshola et al., Journal of the American Oil Chemists Society, 1996, 73, 255-257.
G.L. Pardo Andreu et al., European Journal of Pharmacology 2010, 635,124-128.
S. Germezgoli et al., SJIMU 2015, 22(6), 34-43.
"Nutrition and Health Benefits of Tiger Nuts (Yellow nutgrass, Chufa, *Cyperus esculentus*)". By Inform Africa (http://www.informafrica.com/author/informafrica/) on May 10, 2012—1 Comment (http://www.informafrica.com/healthafrica/nutritionandhealthbenefitsoftigernutsyellownutgrasschufacyperusesculentus/# comments), Feb. 16, 2016.
Dimitrov, et al., "Acute Toxicity, Antidepressive and Mao Inhibitory Activity of Mangiferin Isolated From Hypericum Aucheri", Biotechnol. & Biotechnol. Eq. 2011, 25(4), 2668-2671.
Dimpfel, "Drug Discovery and Translational Medicine—Neurophysiological Techniques Provide a Holistic Approach to Saving Animals", Freienbrink Herstellung und Verlag. ISBN: 978-3-7386-7039-4, pp. 47-54 (2015).
Karababa, "Chemical Composition and Technological Evaluation fo Chufa Tuber (*Cyperus esculentus* L.)", GIDA (2001) 26(4):243-246.
Linssen, et al., "Chufa (*Cyperus esculentus*): A New Source of Dietary Fibre", J Sci Food Agric 1989, 49, 291-296.
Muruganandan, "Effect of mangiferin on hyperglycemia and atherogenicity in streptozotocin diabetic rats", Journal of Ethnopharmacology 97 (2005) 497-501.
Papadelis, et al., "Indicators of Sleepiness in an Ambulatory EEG Study of Night Driving", Proceedings of the 29th IEEE, EMBS Annual International Conference, New York City, USA, Aug. 30-Sep. 3, 2006, pp. 6201-6204.
Rosengarten, Jr., "Tiger Nuts", The Book of Edible Nuts, Roasted Whole Soy Flour & Soy Coffee, New York, NY, Walker and Company p. 330-332 (1984) p. 528.
Sederberg, et al., "Hippocampal and Neocortical Gamma Oscillations Predict Memory Formation in Humans", Cerebral Cortex May 2007, 17:1190-1196, Advance Access publication Jul. 10, 2006.
Sheik, et al., Current Research in Neuroscience, 5(1): 10-19 (2015).
Iwa, "Cyperus Esculentus" in Handbook of African Medicinal Plants, pp. 1-239. (2013).
Kumar, et al. Journal of Environmental Biology. 30(4) 563-566. (2009).

* cited by examiner

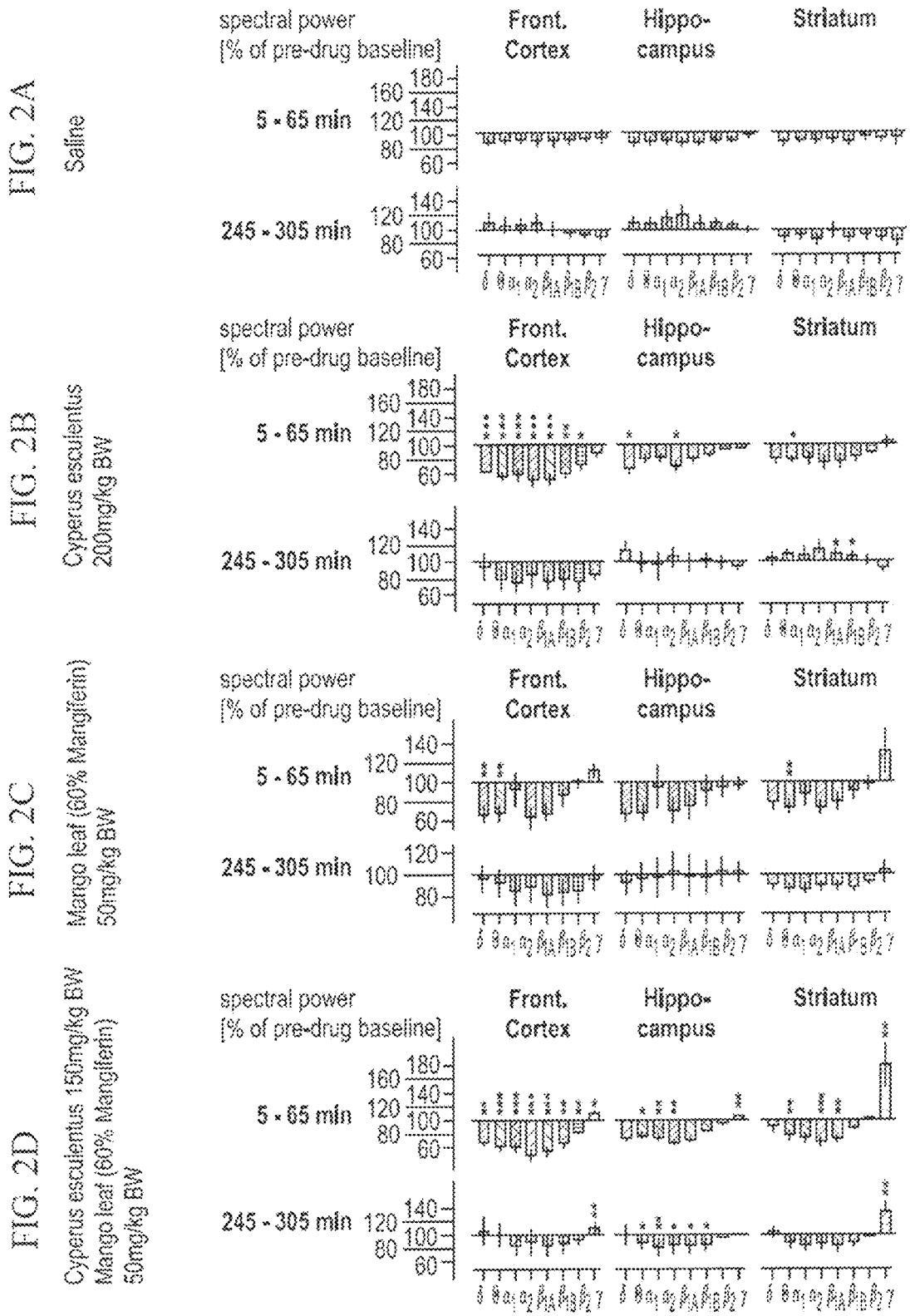

MANGIFERIN-CONTAINING COMPOSITIONS FOR IMPROVING SPORTS PERFORMANCE

CROSS-REFERENCE TO RELATED APPLICATIONS

This application is a continuation-in-part of parent U.S. application Ser. No. 15/214,263, filed on Jul. 19, 2016. The entire disclosure of the prior application is hereby incorporated by reference in its entirety.

BACKGROUND

Technical Field

This disclosure relates generally to compositions which enhance brain activities and prevent drowsiness without causing undesired physical or psychological side effects. This invention further relates to compositions which mimic the activity of caffeine on the brain without the side-effects of caffeine, and to their use as a caffeine replacement.

Description of Related Art

This disclosure relates to a composition that increases attention, alertness, concentration and memory and serves as a substitute or reducer of caffeine or theobromine in energy enhancing products and compositions. This new combination contains a plant extract of Tigernut, also known as Chufa (*Cyperus esculentus*), and an extract containing mangiferin which might be of different origin. For example, the mangiferin—containing extract might be a Mango leaf extract, a Honey bush tea extract, or an extract of coffee leaves.

In stressful or tiring situations, people frequently feel exhausted, depressed and tired and need a sustained boost of energy to increase concentration, attention, alertness and mood. Mainly because of the alertness and mental energy enhancing effect provided by the caffeine and theobromine contained in coffee and cacao, 2.1 billion cups of coffee are consumed per day and 7.2 million tons of chocolate per year worldwide. These stimulants of the Central Nervous System (CNS) are used by athletes and military personnel to increase alertness and concentration, endurance, performance, reaction time and the intensity of training session, and to reduce drowsiness of shift workers and by students in schools and universities to improve concentration, learning and memory, and to enhance mood and control stress. Desired effects of the composition begin approximately half to one hour after consumption, and the effect experienced from a moderate dose usually subsides in about three or four hours. A cup of coffee typically contains 80-175 mg of caffeine, depending on how the coffee is prepared, the source, e.g., brand, of fresh or instant coffee, or the variety of "bean" (seed) used. Additionally, CNS stimulants, including caffeine, can result in significant improvements in sports performance, including in training and endurance.

However, caffeine is also addictive and, like other products containing caffeine such as chocolate and cola, which are consumed in large quantities and included in energy enhancing products, excessive caffeine consumption is related to serious health concerns. The excessive use of caffeine or theobromine causes nervousness, agitation, arrhythmias, bradycardia, tachycardia, increased blood pressure and vasoconstriction, leading to mild anxiety, jitteriness, insomnia, increased sleep latency and reduced coordination. Due to these side effects, for example, the UK Food Standards Agency recommends that pregnant women should limit their caffeine intake, out of prudence, to less than 200 mg of caffeine a day—the equivalent of two cups of instant coffee, or one and a half to two cups of fresh coffee.

Neurotransmitter receptors and transporters represent main targets of drugs in the central nervous system. Interaction of drugs with these molecules induces a signaling cascade, which finally results in the control of ion channel conductance. Since the electric activity of single neurons depends on the set of momentarily active ion channels, communication between neurons is governed by channel activity. Electrical field potentials of the brain reflect the nett electrical information from larger local networks of electrically active neurons, by representing the interaction of drugs with their targets within the concert of neurotransmission including complex modulation from feedback loops. Frequency analysis of the field potentials in the presence of drugs leads to the so-called electropharmacogram, which has been widely used to characterize drug actions on rat and human brains. Comparison of the electropharmacograms of novel compositions can be made with the electropharmacograms of reference pharmaceuticals and botanicals, since similarity of electropharmacogram between novel composition and reference compounds indicates similarity in CNS activity, and enables understanding of the health applications of the composition in humans. Dimpfel, W. 2015. *Drug Discovery and Translational Medicine*. Freienbrink Herstellung und Verlag. ISBN: 978-3-7386-7039-4, pp. 47-54.

CNS stimulants have been demonstrated to influence brain wave activity. It is well known in the art that the attenuation or stimulation pattern, and type of brain wave activity reflects underlying brain activities including alertness, attention, concentration, and the anatomical location of the activity can also be related to specific brain functions, for example activation of memory through activation of the hippocampus. Sleepiness and/or fatigue, for example, have been shown to be correlated to a significant increase of alpha wave activity and a decrease of gamma wave activity. Papadelis et al., *Proceedings of the 28th IEEEEMBS Annual International Conference*, New York City, USA, Aug. 30-Sep. 3, 2006, pp. 6201-6204. Increased gamma-band EEG activity is associated with states of high arousal, alertness, or attention. Decreases in alpha- and beta-activity in the EEG generally correlate to an increase in neurotransmission, resulting in increased alertness.

Increased gamma wave activity in the brain has been shown to correlate to successful memory formation. Increases in alpha wave activity, in contrast, have been shown to correlate to decreased memory performance. Sederberg et al., *Cerebral Cortex*, Vol. 17, pp. 1190-1196 (2007). Since the hippocampus is involved in transmitting information from short-term memory to long-term memory, CNS stimulants which increase gamma activity in the hippocampus and/or reduce alpha activity in the hippocampus are desirable for increasing long-term memory.

Pyramidal cell activity is also correlated with cognitive function. Pyramidal cells, or pyramidal neurons, are multipolar neurons found in the cerebral cortex, the hippocampus, and the Pyramidal neurons have have been linked to neuroplasticity and cognition. Pyramidal cells have conic shaped soma, or cell bodies. An apical dendrite rises from the apex of the soma. The apical dendrite branches several times as it extends towards the cortical surface. Basal dendrites arise from the base of the soma. As distance increases from the soma, the basal dendrites branch profusely.

Dendritic spines receive most of the excitatory impulses (EPSPs) that enter a pyramidal cell. Dendritic spines increase the receptive surface area of the neuron. The greater the pyramidal cell's surface area, the greater the neuron's ability to process and integrate large amounts of information. The typical apical dendrite in a human may have 6,000 dendritic spines or more.

Pyramidal neurons in the prefrontal cortex are implicated in cognitive ability. In mammals, the complexity of pyramidal cells increases from posterior to anterior brain regions. The degree of complexity of pyramidal neurons is likely linked to the cognitive capabilities of different anthropoid species. As the prefrontal cortex receives input from areas of the brain that are involved in processing all the sensory modalities, pyramidal cells within the prefrontal cortex appear to process different types of input. Pyramidal cells may play a critical role in complex object recognition within the visual processing areas of the cortex.

The present disclosure provides compositions useful for replacing or reducing caffeine/theobromine levels in food or beverages while retaining the alertness, attention, concentration and memory benefits of caffeine/theobromine. The compositions disclosed herein do not cause nervousness, anxiety, agitation, arrhythmia, bradycardia, tachycardia, increased blood pressure or vasoconstriction, but do offer the CNS-activating effects associated with caffeine or theobromine. The present disclosure also provides compositions useful for stimulating pyramidal cell function.

The compositions disclosed herein provide increased alertness, attention, focus and well-being over a relatively extended period of time, but are substantially free of side effects and have no addictive potential, so they can be consumed long-term in any person or mammal.

The compositions disclosed herein may be used to provide food and beverage products including shakes, smoothies, beverages, chocolate and energy-drinks with alertness enhancing qualities without the known drawbacks of caffeine or theobromine.

The foregoing objects and advantages of the invention are illustrative of those that can be achieved by the various exemplary embodiments and are not intended to be exhaustive or limiting of the possible advantages that can be realized. Thus, these and other objects and advantages of the various exemplary embodiments will be apparent from the description herein or can be learned from practicing the various exemplary embodiments, both as embodied herein or as modified in view of any variation that may be apparent to those skilled in the art. Accordingly, the present invention resides in the novel methods, arrangements, combinations, and improvements herein shown and described in various exemplary embodiments.

SUMMARY

In light of the present need for substitutes for caffeine and related compounds, a brief summary of various disclosed embodiments is presented. Some simplifications and omissions may be made in the following summary, which is intended to highlight and introduce some aspects of the disclosed subject matter, but not to limit the scope of the invention. Detailed descriptions of preferred embodiments, adequate to allow those of ordinary skill in the art to make and use the inventive concepts, will follow in later sections.

Various embodiments disclosed herein relate to a combination of two natural products for caffeine replacement or reduction, containing an extract of *Cyperus esculentus* and mangiferin. The combination has an effect comparable to the CNS stimulant effect provided by caffeine or theobromine, but does not possess the negative drawbacks of caffeine or theobromine. This combination is not addictive. It can be combined with numerous natural compounds or plant extracts for additional benefits, or flavoring or can be added into existing formats, formulations and food products in several ways, being for example a liquid or a powder, granules, a gum or a sachet.

The ingredients of the described invention are a water or ethanolic extract of whole Tigernut or Tigernut peel, and pure mangiferin or a plant extract standardized to mangiferin, derived by extraction of, for example, mango leaves, mango fruit, or honey bush tea. These products can form part of different products and can be combined in different ratios and added to other ingredients.

Various embodiments disclosed herein relate to methods for enhancing at least one of alertness, attention, concentration, and memory in a person in need thereof, by administering an herbal composition to said person. The herbal composition may comprise an effective amount of an extract of *Cyperus esculentus* peel, *Cyperus esculentus* rhizomes, or a combination thereof. In some embodiments, the herbal composition may comprise an effective amount of mangiferin, norathyriol, or an extract comprising mangiferin or norathyriol. In other embodiments, the herbal composition may comprise a mixture of an effective amount of an extract of *Cyperus esculentus* peel, *Cyperus esculentus* rhizomes, or a combination thereof; and an effective amount of mangiferin, norathyriol, or an extract comprising mangiferin or norathyriol.

In various embodiments, the extract of *Cyperus esculentus* peel and/or *Cyperus esculentus* rhizomes, or a combination thereof is an aqueous extract, an alcoholic extract, or a hydro alcoholic extract. The extract of *Cyperus esculentus* may be a hydro alcoholic extract of peel of *Cyperus esculentus* rhizomes. The extract of *Cyperus esculentus* peel and/or *Cyperus esculentus* rhizomes may be used in an amount of between 20 mg and 20 g per dose.

In various embodiments, the herbal composition contains mangiferin, norathyriol, or an extract comprising mangiferin or norathyriol, used in an amount of between 20 mg and 5 g per dose. In some embodiments, the herbal composition contains an extract comprising mangiferin or norathyriol in an amount sufficient to provide between 20 mg and 5 g mangiferin or norathyriol per dose. The extract comprising mangiferin or norathyriol may be a mangiferin-containing extract of a plant species in a genus selected from the group consisting of *Mangifera, Salacia, Cyclopia, Hypericum, Canscora, Fagraea, Gentiana, Hoppea, Coffea, Swertia, Hypericum, Polygala, Zizyphus, Coffea*, and mixtures thereof.

Various embodiments disclosed herein relate to methods for enhancing at least one of alertness, attention, concentration and memory in a person in need thereof, by administering a herbal composition to said person, by administering a mixture of an effective amount of:
  a) an extract of *Cyperus esculentus* peel, *Cyperus esculentus* rhizomes, or a combination thereof; and
  b) an effective amount of mangiferin or an extract comprising mangiferin, where the ratio of (a) to (b) is between about 1:1 and about 50:1, about 1:1 and 30:1, about 2:1 and 25:1, about 1:1 and 20:1, about 4:1 and 15:1, about 10:1 and 15:1, or about 12:1. In various embodiments, the effective amount of (a) is between 20 mg and 20 g per dose; and the effective amount of said mangiferin or said mangiferin-containing extract is between 5 mg and 5 g per dose. In some embodiments, the mixture of (a) and (b) is provided as a unit dose containing between about 10 mg and about 20 g per dose.

In various embodiments, the herbal compositions disclosed herein contain:
a) a herbal composition comprising:
 i. an extract of *Cyperus esculentus* peel, *Cyperus esculentus* rhizomes, or a combination thereof;
 ii. an effective amount of mangiferin or an extract comprising mangiferin; or
 iii. a mixture of (i) and (ii); in combination with:
b) an active ingredient selected from the group consisting of B group vitamins, caffeine, citicoline, citrulline, choline, curcumin, huperzine, luteolin, ibogaine, magnesium, N-methyltyramine, oleamide, omega-3 fatty acids, octopamine, phosphatidlyserine, phosphatidlyserine, quercetin, rutin, resveratrol, synephrine, taurine, taxifoline, theanine, theobromine, xanthohumol, yangonin, yohimbine, ecdysteroids (20HE) extracts of plant species of the genera *Aframomum, Aloysia, Alpinia, Astragalus, Bacopa, Centella, Citrus, Coca, Cola, Curcuma, Coffea, Celastrus, Camellia, Eleutherococcus, Ephedra, Euterpe, Garcinia, Ginkgo, Ganoderma, Glycyrrhiza, Icarine, Ilex, Irvingia, Kaempferia, Ocimum, Paullinia, Panax, Pfaffia, Piper Pueraria, Rhodiola, Rhaponticum, Sida, Sideritis, Tabernanthe, Theobroma, Vitis, Withania, Zingiber, Zizyphus*, and mixtures thereof.

Various embodiments disclosed herein relate to methods for maintaining the attention, alertness, concentration and memory-enhancing effect of a product comprising caffeine or theobromine, while reducing side effects from the caffeine or theobromine. The method comprises replacing all or part of the caffeine or theobromine in the product with a composition comprising:
a) an effective amount of an extract of *Cyperus esculentus* peel, *Cyperus esculentus* rhizomes, or a combination thereof, where the effective amount may be between about 20 mg and about 20,000 mg, between about 100 mg and about 5000 mg, between about 500 mg and about 4000 mg, or between about 1000 mg and about 3000 mg of the extract;
b) an effective amount of mangiferin, norathyriol, or an extract comprising mangiferin or norathyriol, where the effective amount may be between about 1 mg and about 50 mg, between about 1 mg and about 35 mg, between about 1 and about 20 mg, between about 5 and about 15 mg, or between about 8 and about 12 mg of the extract; or
c) a synergistic mixture of (a) and (b). In various embodiments, each milligram of caffeine or theobromine removed from the product comprising caffeine or theobromine is replaced by between 20 mg and 200 mg of the extract of *Cyperus esculentus* peel and/or rhizomes, and/or between 1 and 20 mg of mangiferin, norathyriol, or a botanical extract comprising mangiferin or norathyriol.

In various embodiments, "a botanical extract comprising mangiferin or norathyriol" may be standardized to a defined content of mangiferin or norathyriol, where the defined content of mangiferin or norathyriol is from 10% to 99% by weight of the extract, from 20% to 95% by weight of the extract, from 30% to 90% by weight of the extract, from 40% to 80% by weight of the extract, from 50% to 70% by weight of the extract, from 55% to 65% by weight of the extract, or about 60% by weight of the extract.

In various embodiments, "a botanical extract comprising mangiferin or norathyriol" may be an extract of a plant or plant part from a species containing mangiferin and/or norathyriol, and may be obtained by extraction of the plant or plant part with water, an aqueous base, a polar protic organic solvent, a polar aprotic organic solvent, or a mixture thereof. In various embodiments, the plant species comprises mangiferin, and is extracted with water, a lower alcohol having 1 to 4 carbon atoms, or a mixture thereof to produce a botanical extract comprising mangiferin, optionally standardized to a defined percentage of the botanical extract.

Various embodiments disclosed herein relate to methods for enhancing sports performance through administration of a composition comprising:
a) an effective amount of an extract of *Cyperus esculentus* peel, *Cyperus esculentus* rhizomes, or a combination thereof, where the effective amount may be between about 20 mg and about 20,000 mg, between about 100 mg and about 5000 mg, between about 500 mg and about 4000 mg, or between about 1000 mg and about 3000 mg of the extract;
b) an effective amount of mangiferin, norathyriol, or a botanical extract comprising mangiferin or norathyriol, where the botanical extract comprising mangiferin or norathyriol is optionally standardized to a defined content of mangiferin or norathyriol,
 where the effective amount may be between about 1 mg and about 50 mg, between about 1 mg and about 35 mg, between about 1 and about 20 mg, between about 5 and about 15 mg, or between about 8 and about 12 mg of mangiferin, norathyriol, or the botanical extract comprising mangiferin or norathyriol; or
c) a synergistic mixture of (a) and (b). In various embodiments, each milligram of caffeine or theobromine removed from the product comprising caffeine or theobromine is replaced by between 20 mg and 200 mg of the extract of *Cyperus esculentus* peel and/or rhizomes, and/or between 1 and 20 mg of mangiferin, norathyriol, or a botanical extract comprising mangiferin or norathyriol.

Either or both of chufa and mangiferin can be used to replace or reduce caffeine in sports performance products. Both extracts are anticipated, through enhancing attention, alertness, and reaction time to have sports performance-enhancing activities. These extracts are expected to enhance concentration and endurance in much the same manner as caffeine. However, these extracts have been demonstrated to lack the undesirable side effects associated with caffeine.

Additionally, various embodiments disclosed herein relate to methods for enhancing memory and/or increasing central nervous system activity in a person in need thereof, by administering to the person:
a) an effective amount of mangiferin, norathyriol, or an extract comprising mangiferin or norathyriol; and
b) an effective amount of caffeine;
 wherein the mangiferin, norathyriol, or the botanical extract comprising mangiferin or norathyriol and the caffeine synergistically enhance brain wave activity. The step of administering, according to certain embodiments, comprises administering a single composition comprising an effective amount of mangiferin or a botanical extract comprising mangiferin; and an effective amount of caffeine. Alternatively, the step of administering may comprise administering a first composition comprising an effective amount of mangiferin or a botanical extract comprising mangiferin; and a second composition comprising an effective amount of caffeine, where the first and second compositions may be administered simultaneously or at different times.

In some embodiments disclosed herein, the method comprises co-administering:
a) an effective amount of mangiferin, norathyriol, or an extract comprising mangiferin or norathyriol;
b) an effective amount of caffeine; and
c) an effective amount of an extract of *Cyperus esculentus* peel, *Cyperus esculentus* rhizomes, or a combination thereof.

The step of administering may comprises administering a single composition comprising:
an effective amount of mangiferin or an extract comprising mangiferin;
an effective amount of caffeine; and
an effective amount of an extract of *Cyperus esculentus* peel, *Cyperus esculentus* rhizomes, or a combination thereof, where the *Cyperus esculentus* extract may be a hydroalcoholic extract.

Alternatively, the step of administering may comprise administering a first composition comprising an effective amount of mangiferin or an extract comprising mangiferin; a second composition comprising an effective amount of caffeine; and a third composition comprising an effective amount of an extract of *Cyperus esculentus* peel, *Cyperus esculentus* rhizomes, or a combination thereof. In some embodiments, an extract of *Cyperus esculentus* peel, *Cyperus esculentus* rhizomes, or a combination thereof may be included with either or both of the first composition comprising an effective amount of mangiferin or an extract comprising mangiferin; or the second composition comprising an effective amount of caffeine.

Various embodiments disclosed herein relate to methods for enhancing memory and/or increasing central nervous system activity in a person in need thereof, by administering to the person an effective amount of mangiferin or norathyriol; and an effective amount of caffeine, where the effective amount of the mangiferin or said norathyriol is between 15 mg and 20 g per dose. Various embodiments relate to methods for enhancing memory and/or increasing central nervous system activity in a person in need thereof, by administering to the person an effective amount of a botanical extract comprising mangiferin or norathyriol; and an effective amount of caffeine, where the defined mangiferin or norathyriol content is between 15 mg and 20 g per dose. The effective amount of the botanical extract standardized to a defined mangiferin or norathyriol content is sufficient to provide between 15 mg and 20 g mangiferin or norathyriol per dose. The botanical extract comprising mangiferin or norathyriol is optionally standardized to a defined content of mangiferin or norathyriol, where the defined content of mangiferin or norathyriol is from 10% to 99% by weight of the extract, from 20% to 95% by weight of the extract, from 30% to 90% by weight of the extract, from 40% to 80% by weight of the extract, from 50% to 70% by weight of the extract, from 55% to 65% by weight of the extract, or about 60% by weight of the extract.

The botanical extract comprising mangiferin or norathyriol may be a mangiferin-containing extract of a plant species in a genus selected from the group consisting of *Mangifera, Salacia, Cyclopia, Hypericum, Canscora, Fagraea, Gentiana, Hoppea, Swertia, Hypericum, Polygala, Zizyphus*, and mixtures thereof.

Various embodiments disclosed herein relate to methods for enhancing memory and/or increasing central nervous system activity in a person in need thereof, by administering to the person an effective amount of (a) mangiferin, norathyriol, or an extract comprising mangiferin or norathyriol; and (b) an effective amount of caffeine, in a ratio of (a) to (b) of between about 20:1 and about 200:1, between about 40:1 and about 150:1, or between about 50:1 and about 100:1. In various embodiments, the effective amount of (a) is between 15 mg and 20 g per dose; and said effective amount of caffeine is between 0.1 mg and 1 g per dose.

Various embodiments disclosed herein relate to methods for enhancing memory and/or increasing central nervous system activity in a person in need thereof, by administering to the person an effective amount of (a) mangiferin, norathyriol, or an extract comprising mangiferin or norathyriol; (b) an effective amount of caffeine; and (c) an active ingredient selected from the group consisting of B group vitamins, citicoline, citrulline, choline, phosphatidylcholine, curcumin, huperzine, luteolin, ibogaine, magnesium, N-methyltyramine, omega-3 fatty acids, octopamine, phosphatidlyserine, phosphatidylserine, quercetin, rutin, resveratrol, synephrine, taurine, taxifoline, theanine, theobromine, xanthohumol, yangonin, yohimbine, ecdysteroids (20HE) extracts of plant species of the genera *Aloysia, Alpinia, Astragalus, Bacopa, Centella, Citrus, Coca, Cola, Curcuma, Coffea, Celastrus, Camellia, Eleutherococcus, Ephedra, Euterpe, Garcinia, Ginkgo, Ganoderma, Glycyrrhiza, Icarine, Ilex, Kaempferia, Ocimum, Paullinia, Panax, Pfaffia, Piper Pueraria, Rhodiola, Rhaponticum, Sida, Sideritis, Tabernanthe, Theobroma, Vitis, Withania, Zingiber, Zizyphus*, and mixtures thereof.

BRIEF DESCRIPTION OF THE DRAWINGS

In order to better understand various exemplary embodiments, reference is made to the accompanying drawings, wherein:

FIGS. 2A to 2D show the impact on the neural activity in the frontal cortex, hippocampus, and striatum of saline control (FIG. 2A), *Cyperus esculentus* tuberous rhizome, 30% ethanol extract (FIG. 2B), Mango leaf extract containing 60% Mangiferin (FIG. 2C) and a mixture of *Cyperus esculentus* tuberous rhizome, 30% ethanol extract, and Mango leaf extract containing 60% Mangiferin (FIG. 2D);

Figure 1:
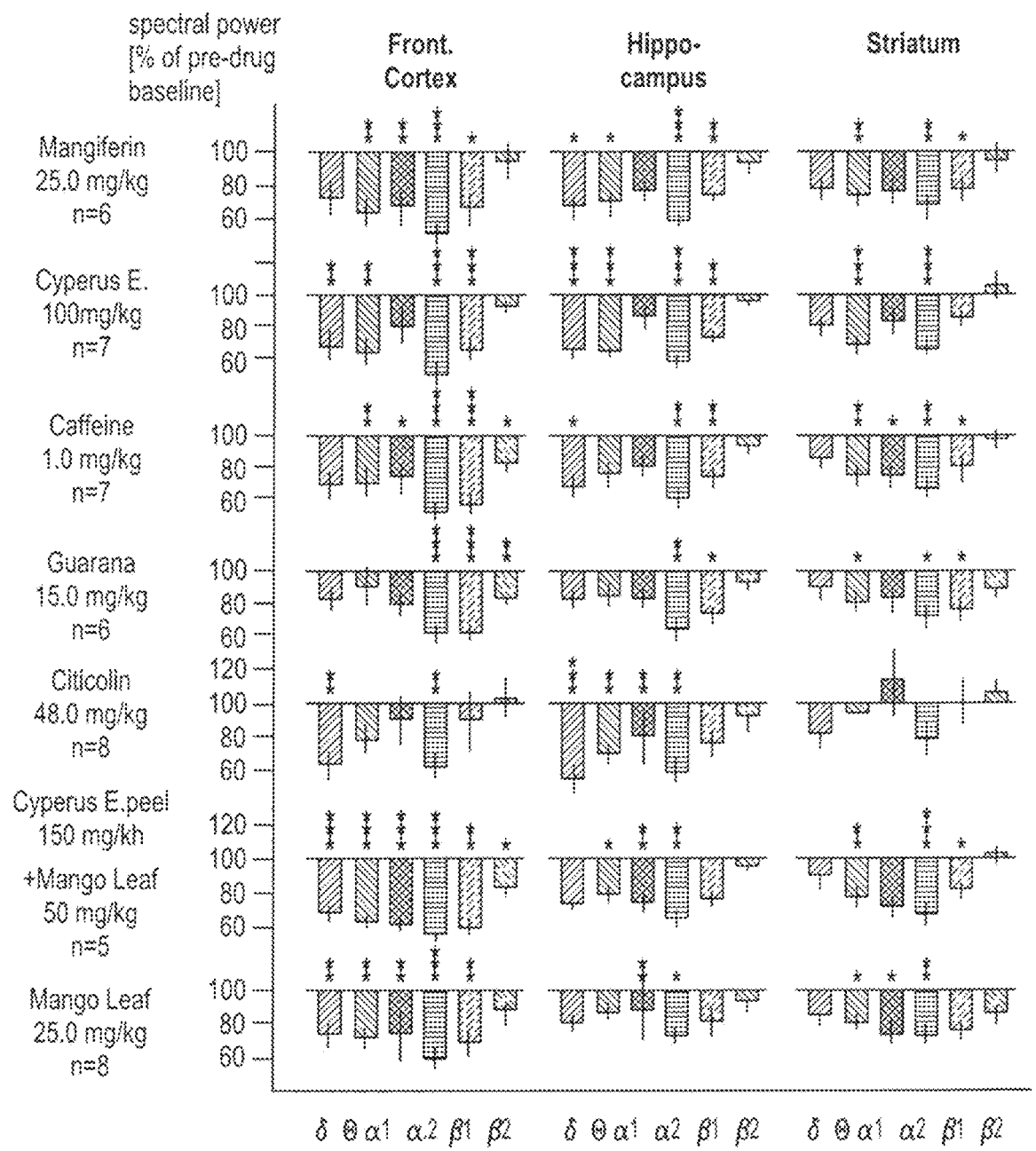
FIG. 1 shows encephalographic (EEG) studies on the combination of *Cyperus esculentus* peel, 30% ethanol extract (150 mg/kg), and Mango leaf extract (60% Mangiferin; 25 mg/kg); Mango leaf extract (60% Mangiferin; 25 mg/kg); *Cyperus esculentus* peel, 30% ethanol extract (100 mg/kg); caffeine (1 mg/kg); Guarana (15 mg/kg); Citicolin (48 mg/kg); and Mangiferin (25 mg/kg)

In the figures, statistical significance is represented in terms of p-values, as follows:

p<0.10: *.
p<0.05: **.
p<0.01: ***.

DETAILED DESCRIPTION

The current disclosure relates to herbal compositions for enhancing at least one of alertness, attention, concentration and memory in a person in need thereof, comprising administering a composition to said person, where the composition comprises:
a) an effective amount of an extract of *Cyperus esculentus*;
b) an effective amount of mangiferin, norathyriol, or an extract comprising mangiferin or norathyriol; or
c) a synergistic combination of (a) and (b).

The current disclosure also relates to enhancing at least one of alertness, attention, concentration and memory in a person in need thereof, comprising co-administering to the person:
an effective amount of mangiferin, norathyriol, or an extract comprising mangiferin or norathyriol; and
caffeine.

The component comprising mangiferin and/or norathyriol and the caffeine may be co-administered in a single composition, or administered in separate compositions.

In the current disclosure, the term "about" encompasses normal variability in the recited amounts. In the context of an effective amount of a biologically active ingredient, the term "about" means that the actual amount of a dosage form is between 80% and 125%, between 90% and 110%, or between 95% and 105% of a stated value. In the context of a ratio between biologically active ingredients, the term "about" means±20%, ±10%, or ±5% of the stated value.

In the current application, the term "a person in need thereof" refers to any person or human subject in need of improved alertness, attention, concentration, and/or enhanced memory. Such person or human subjects may be children, adolescents, adults, or elderly persons. Such person or human subjects may be athletes in need of improving athletic performance. Persons in need of treatment or supplementation to provide improved alertness, attention and concentration may be shift workers, medical personnel, military personnel, long distance drivers, people with Attention Deficit Disorder, or people with Attention Deficit Hyperactivity Disorder. Persons in need of treatment to provide improved memory may be persons suffering from cognitive decline in healthy aging, Mild Cognitive Impairment, dementia, Alzheimer's disease, or Parkinson's disease.

Various embodiments disclosed herein relate to herbal compositions for enhancing alertness, attention, concentration and/or memory, comprising an effective amount of an extract of *Cyperus esculentus*. The extract of *Cyperus esculentus* may be an extract of the entire plant, or of any plant part. The plant part of *Cyperus esculentus* to be extracted may be the leaf, peel, root, rhizome, stem, tuber, or a combination thereof. The extract of *Cyperus esculentus* may be an extract of *Cyperus esculentus* peel, *Cyperus esculentus* rhizomes, a peel derived from *Cyperus esculentus* rhizomes, or a combination thereof. The plant part of *Cyperus esculentus* may be extracted with water, an organic solvent, or a mixture thereof, or by subcritical or supercritical carbon dioxide. The organic extraction solvent may be a polar aprotic solvent, such as DMSO, acetone, or a mixture thereof; or a polar protic solvent, such as a lower alcohol having from 1 to 4 carbon atoms. In various embodiments, the extract of *Cyperus esculentus* is an extract of *Cyperus esculentus* peel, *Cyperus esculentus* rhizomes, a peel derived from *Cyperus esculentus* rhizomes, or a combination thereof, derived by extraction with water, a lower alcohol having from 1 to 4 carbon atoms, or a mixture thereof. In some embodiments, the extract of *Cyperus esculentus* is an extract of *Cyperus esculentus* peel, *Cyperus esculentus* rhizomes, a peel derived from *Cyperus esculentus* rhizomes, derived by extraction with a hydroalcoholic mixture of water and ethanol.

Various embodiments disclosed herein relate to herbal compositions for enhancing alertness, attention, concentration, and/or memory, comprising mangiferin or norathyriol. Mangiferin has a structure of formula Ia, where R is a 1,5-anhydro-D-glucitol ring. Norathyriol is an aglycone of mangiferin, and has a structure of formula Ib, where R is hydroxyl. Unless otherwise stated, the term mangiferin is here defined as encompassing:
mangiferin as a pure compound, where "pure" is defined as meaning the compound is at least 90% mangiferin, at least 95% mangiferin, at least 98% mangiferin, or at least 99.5% mangiferin; or
a composition comprising at least 90% by weight of a mixture of mangiferin and norathyriol.

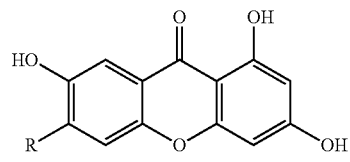

Ia: R = 1,5-anhydro-D-glucitol
Ib: R = —OH

Mangiferin is a xanthonoid polyphenol. Mangiferin is found in several botanicals, including extracts of mango fruit, mango peel, mango bark, mango leaf, as well as in Cyclopia species (Honeybush tea) and species in the genus Salacia. Mangiferin has acetylcholinesterase inhibiting activity, an activity useful in improving cognitive function in Alzheimer's disease.

Mangiferin, a xanthonoid, is a natural phenolic compound formed from the xanthone backbone. If we refer to Mangiferin, its aglycone norathyriol is always included as an alternative ingredient. Mangiferin is an antioxidant and anti-inflammatory that has been shown to exhibit various pharmacological activities, including anti-diabetic, anti-cancer, and anti-oxidant effects as well as anti-inflammatory, anti-viral, immune-modulatory and anti-microbial activities. Prevention of stress-induced effects related to neurodegenerative diseases, reduction of neurological brain deficits and a positive effect on injured neurons has been reported with mangiferin, indicating that mangiferin may play a role in pathologies related to neuroinflammation and oxidative damage. Mangiferin may also enhance recognition memory and improve memory deficits, while the inhibition of $MAO_A$ seems to be responsible for its anti-depressant-like effect. No effects indicating an increase of attention, alertness, concentration, reaction time or wellbeing have been described in the literature Mangiferin of the invention is preferably extracted from a plant containing Mangiferin. Excellent sources of the desired material are *Mangifera Indica* (bark, fruit or leaf) or Honey bush tea, which are preferably standardized to a concentration of 20-70% mangiferin, depending on the raw material. But it can be obtained from other sources, including plant species of the genera *Mangifera, Salacia, Cyclopia, Hypericum, Canscora, Fagraea, Gentiana, Hoppea, Coffea, Swertia, Hypericum, Polygala, Zizyphus*, and *Coffea*.

Tigernut (*Cyperus esculentus*), a crop of the sedge family widespread across the world, is a typical Spanish food found on markets and in the supermarket. In Spain, the milky extract of Tigernut (i.e., "horchata de chufa"), a non-alcoholic beverage, has an annual economic impact of 60 million Euro. Tigernut is rich in fiber, proteins, sugars, oleic acid and glucose, as well as in phosphorus, potassium, and vitamins C and E. Tigernut is useful for enhancing blood circulation, preventing heart disease, and reducing the risk of colon cancer. No attention, alertness, concentration or memory increasing effect of chufa has been described in the scientific literature.

Whole Tigernut and Tigernut peel aqueous and 30% ethanolic extracts contain high amounts of fat and carbohydrates, but no detectable alkaloids or flavonoids. The extracts have a very pleasant and sweet taste, so that no restriction due to taste has to be made. Oral ingestion of 4 g of Tigernut extract provides a smooth increase in mental energy as well as a calming effect.

It has now been found in accordance with the present invention that the combination of Tigernut and Mangiferin serves to moderate the bitter taste and unusual flavor of Mangiferin. Furthermore, the electropharmacogram of the combination looks strikingly similar to the electropharmacogram of caffeine (FIG. 1). Gamma waves, related to alertness, attention, and memory (FIG. 2D), were increased synergistically 20-30 minutes after oral ingestion of the combination. While gamma waves can also relate to motion, motion sensors showed no change in motion, so the increase in gamma waves can be related to alertness, attention and memory. This effect on gamma waves lasted for the surprisingly long duration of 5 hours and was only seen in the combination; such increases were not observed upon administration of *Cyperus esculentus* tuberous rhizome extract alone (FIG. 2B) or mangiferin alone (FIG. 2C). No secondary effects comparable to those usually related to caffeine were observed in a human study (n=9). Besides, the invention resulted in a synergistic attenuation of Hippocampus brain waves, representing an activation of neurotransmission, as shown in rats (FIG. 2D).

Mangiferin and its aglycone metabolite norathyriol may be included in the disclosed compositions as pure compounds, or as components of an extract of a plant species in a genus selected from the group consisting of *Mangifera, Salacia, Cyclopia, Hypericum, Canscora, Fagraea, Gentiana, Hoppea, Coffea, Swertia, Hypericum, Polygala, Zizyphus, Coffea* and mixtures thereof. The plant species contain mangiferin and/or norathyriol, and may be extracted with water, an aqueous base, a polar protic organic solvent, a polar aprotic organic solvent, or a mixture thereof. In various embodiments, the plant species comprises mangiferin, and is extracted with water, a lower alcohol having 1 to 4 carbon atoms, or a mixture thereof.

In various embodiments, the herbal composition contains mangiferin, norathyriol, or an extract comprising mangiferin or norathyriol, used in an amount of between 20 mg and 5 g per dose. The herbal composition may contain an extract comprising mangiferin or norathyriol of between 20 mg and 5 g per dose. If the concentration of mangiferin and/or norathyriol in the extract is known, the extract may be provided in an amount sufficient to provide between 20 mg and 5 g mangiferin or norathyriol per dose. Thus, for example, if an extract of a plant of the genus *Mangifera* contains 30% mangiferin, the extract may be provided in an amount of between 20 mg and 5 g per dose, based on the weight of the extract. Alternatively, the *Mangifera* extract may be administered in an amount of between 66.7 mg and 16.7 grams per dose, thus providing between 20 mg and 5 g mangiferin per dose.

Various disclosed embodiments relate to herbal compositions containing Chufa or Tigernut extracts and mangiferin-containing botanical extracts, where the compositions are effective in enhancing CNS activity in the frontal cortex, hippocampus, striatum, and/or reticular formation. In various embodiments, the compositions are effective for enhancing memory, as shown by increased gamma wave activity in the brain, coupled with decreased alpha wave activity. The compositions are also effective for increasing alertness and attention, as shown by decreases in alpha- and beta-activity and increased gamma wave activity in the EEG.

Through animal encephalographic (EEG) studies, the current application demonstrates that Chufa or Tigernut extracts (prepared by extraction of *Cyperus esculentus* tuberous rhizome) and mangiferin (as pure compound) and mangiferin-containing botanical extracts are strikingly similar in CNS profile to each other. Further, they are surprisingly similar in activity to the known CNS stimulants caffeine, guarana (a caffeine-containing botanical extract of *Paulinia cupana*), cytidine 5'-diphosphocholine, also known as citicoline, (a nootropic). Chufa extracts are less potent than mangiferin. In a human adult subject, about 4 grams of chufa extract has about the same activity as about 400 mg mangiferin.

The key discoveries presented herein are that *Cyperus esculentus* extracts and mangiferin have a very similar CNS activating effect (as evidenced by EEG) to each other and to caffeine. However, unlike caffeine, *Cyperus esculentus* extracts and mangiferin also exhibit a calming, de-stressing activity when ingested. Further, *Cyperus esculentus* extracts and mangiferin exhibit a plateau effect. Beyond a certain threshold value, an increased intake of these extracts does not give greater CNS stimulation, minimizing abuse potential and potential for side-effects. Even at high servings or doses *Cyperus esculentus* extracts and mangiferin exhibit none of the well-known side-effects, e.g., nausea, fast or irregular pulse, irritability, and loss of concentration, caused by excessive doses of caffeine.

Chufa peels have, in the prior art, generally been considered to be a waste product of Chufa processing. However, it has been discovered that a 30% ethanol-water extract of chufa peels, e.g., peels of Chufa tuberous rhizomes, exhibit more potent activating activity than a 30% ethanol-water extract of whole chufa, which in turn has more potent activity than a water extract of whole chufa. Ethanolic, aqueous, and hydroalcoholic extracts of Chufa tuberous rhizomes all, however, exhibit desirable CNS activating activity.

In various embodiments, Chufa or Tigernut extracts and mangiferin-containing botanical extracts may be taken as individual active ingredients. Chufa or Tigernut extracts are desirably taken by an adult human in an amount of about 0.1 g/day to about 10 g/day, about 0.5 g/day to about 8 g/day, about 1 g/day to about 5 g/day, or about 1 g/day to about 4 g/day. An adult human in an amount of about 25 mg/day desirably takes Mangiferin-containing botanical extracts to about 5 g/day, about 50 mg/day to about 2 g/day, about 100 mg/day to about 1 g/day, or about 200 mg/day to about 400 mg/day.

Chufa or Tigernut extracts and mangiferin-containing botanical extracts have synergistic activity of gamma wave activity in the striatum, and on CNS activity in the hippocampus. The increase in gamma wave activity in the striatum is evidence that the composition increases alertness and attention. The hippocampus belongs to the limbic system and plays an important role in the consolidation of information from short-term memory to long-term memory and spatial navigation. Thus, the pattern of changes in CNS activity in the hippocampus suggest that the disclosed Chufa/mangiferin composition has a beneficial effect on memory. Chufa or Tigernut extracts and mangiferin-containing botanical extracts are desirably combined in a ratio of between about 0.5:1 and about 30:1, about 1:1 and about 20:1, about 5:1 and about 10:1 and about 7.5:1.

Chufa or Tigernut extracts and mangiferin-containing botanical extracts, whether taken separately or together, have a rapid onset of action. Within an hour after oral ingestion, or within 15-20 minutes after buccal mucosal absorption, EEG results show an impact of the extracts on neural activity. The extracts have a long duration of action, of between 3-6 hours. When Chufa or Tigernut extracts and mangiferin-containing botanical extracts are combined and ingested together, the duration of action is at least 5 hours, and the effect of the combination on brain wave activity after 5 hours is significantly greater than the effect on brain wave activity of either extract individually 5 hours after ingestion.

Persons who have ingested Chufa or Tigernut extracts and mangiferin-containing botanical extracts as disclosed herein, taken individually or together, report that the extracts enhance focus and concentration. Persons who have ingested Chufa or Tigernut extracts and mangiferin-containing botanical extracts as disclosed herein, taken individually or together, report that the extracts enhance focus and concentration, improves motivation, and elevates mood, while simultaneously inducing a feeling of calm, reduced anxiety, and reduced stress, tension and nervousness, and reduced impulsivity. Unlike caffeine, even at very high doses the extracts do not produce nervousness, irritability, jitters, lack of concentration, or a fast and irregular pulse.

Chufa or Tigernut extracts and mangiferin-containing botanical extracts as disclosed herein are not bitter, taste pleasant, and are perfectly suited to application in functional foods and beverages. The extracts can be used to reduce or replace caffeine in foods, beverages, and supplements without causing caffeine cravings or withdrawal. As discussed above, the herbal compositions disclosed herein contain a herbal composition comprising:

an extract of *Cyperus esculentus* peel, *Cyperus esculentus* rhizomes, or a combination thereof;
an effective amount of mangiferin or an extract comprising mangiferin; or
a mixture of an extract of *Cyperus esculentus* peel or rhizomes and mangiferin or an extract comprising mangiferin.

The compositions may comprise:
i) from about 10% to about 99.5% by weight, about 25% to about 95% by weight, about 40% to about 90% by weight, or about 50% to about 80% by weight, of an extract of *Cyperus esculentus* peel, *Cyperus esculentus* rhizomes, or a combination thereof; and from about 0.5% to about 90% by weight, about 5% to about 75% by weight, about 10% to about 60% by weight, or about 30% to about 50% by weight of a further ingredient for enhancing mood or decreasing stress or anxiety;
ii) from about 10% to about 99.5% by weight, about 25% to about 95% by weight, about 40% to about 90% by weight, or about 50% to about 80% by weight, of mangiferin or an extract comprising mangiferin; and from about 0.5% to about 90% by weight, about 5% to about 75% by weight, about 10% to about 60% by weight, or about 30% to about 50% by weight of the further ingredient for enhancing mood or decreasing stress or anxiety; or
iii) from about 10% to about 99.5% by weight, about 25% to about 95% by weight, about 40% to about 90% by weight, or about 50% to about 80% by weight, of a mixture of
a. an extract of *Cyperus esculentus* peel and/or rhizomes and
b. mangiferin or a botanical extract comprising mangiferin; and
from about 0.5% to about 90% by weight, about 5% to about 75% by weight, about 10% to about 60% by weight, or about 30% to about 50% by weight of the further ingredient for enhancing mood or decreasing stress or anxiety.

In various embodiments, the further ingredient for enhancing mood or decreasing stress or anxiety is caffeine. In some embodiments, the further ingredient for enhancing mood or decreasing stress or anxiety is selected from the group consisting of B group vitamins, citicoline, citrulline, choline, curcumin, huperzine, luteolin, ibogaine, magnesium, N-methyltyramine, omega-3 fatty acids, octopamine, oleamide, phosphatidlyserine, phosphatidlyserine, quercetin, rutin, resveratrol, synephrine, taurine, taxifoline, theanine, theobromine, xanthohumol, yangonin, yohimbine, ecdysteroids (20HE) extracts of plant species of the genera *Aloysia, Alpinia, Astragalus, Bacopa, Centella, Citrus, Coca, Cola, Curcuma, Coffea, Celastrus, Camellia, Eleutherococcus, Ephedra, Euterpe, Garcinia, Ginkgo, Ganoderma, Glycyrrhiza, Icarine, Ilex, Kaempferia, Melissa, Ocimum, Paullinia, Panax, Pfaffia, Piper, Puer-*

*aria, Rhodiola, Rhaponticum, Sida, Sideritis, Tabernanthe, Theobroma, Vitis, Withania, Valeriana, Zingiber, Zizyphus*, and mixtures thereof.

The further ingredient for enhancing mood or decreasing stress or anxiety may also comprise caffeine in combination with one or more of a B group vitamin, citicoline, citrulline, choline, curcumin, huperzine, luteolin, ibogaine, magnesium, N-methyltyramine, omega-3 fatty acids, octopamine, oleamide, phosphatidlyserine, phosphatidlyserine, quercetin, rutin, resveratrol, synephrine, taurine, taxifoline, theanine, theobromine, xanthohumol, yangonin, yohimbine, ecdysteroids (20HE) extracts of plant species of the genera *Aloysia, Alpinia, Astragalus, Bacopa, Centella, Citrus, Coca, Cola, Curcuma, Coffea, Celastrus, Camellia, Eleutherococcus, Ephedra, Euterpe, Garcinia, Ginkgo, Ganoderma, Glycyrrhiza, Icarine, Ilex, Kaempferia, Melissa, Ocimum, Paullinia, Panax, Pfaffia, Piper, Pueraria, Rhodiola, Rhaponticum, Sida, Sideritis, Tabernanthe, Theobroma, Vitis, Withania, Valeriana, Zingiber*, and *Zizyphus*.

Mangiferin and *Mangifera* extracts may be incorporated into an oral dosage form, including an orally dissolvable or dispersible buccal strip, a chewing gum, a tablet, a capsule, an emulsion, a suspension, an oral spray, effervescent, dissolvable granules or powder, a sachet, or a clear beverage. Chufa extracts, alone or in combination with Mangiferin and *Mangifera* extracts, are typically opaque and milky in beverage form, and may be incorporated into an oral dosage form, including an orally dissolvable or dispersible buccal strip, a chewing gum, a tablet, a capsule, dissolvable granules or powder, a sachet, an emulsion, a suspension, dairy milk, non-dairy milks, yoghurt, and milk-fruit juice combinations.

The compositions disclosed herein may be provided as:
  an orally dissolvable or dispersible buccal strip for mucosal absorption, a chewing gum, a lozenge, an effervescent tablet, a capsule, or an emulsion;
  a functional chocolate, marzipan, or sweetmeat,
  a functional spread in measured doses in a foil sachet, to be spread on bread or crackers;
  a powder with a measuring spoon for addition to any beverage or food;
  an oral or nasal spray;
  a non-dairy creamer in sachet or stick form to add to a beverage; and
  a snack-bar, candy, or cookie.

In some embodiments, the compositions disclosed herein are provided as components of edible emulsions, e.g., mayonnaise, egg-free mayonnaise substitutes, Hollandaise sauce, butter, or margarine. Such emulsions may be used as condiments on food or spreads served with bread or crackers. The emulsions may be prepared by:
  emulsifying an oil phase in a water phase, and then adding mangiferin, an extract containing mangiferin, a Chufa extract, or a mixture thereof to the resulting oil-in-water emulsion;
  emulsifying a water phase in an oil phase, and then adding mangiferin, an extract containing mangiferin, a Chufa extract, or a mixture thereof to the resulting water-in-oil emulsion; or
  emulsifying either a water phase in an oil phase or an oil phase in a water phase to produce an emulsion, and then adding mangiferin, an extract containing mangiferin, a Chufa extract, or a mixture thereof to the emulsion.

The compositions disclosed herein may be may be incorporated into an oral dosage form, including an orally dissolvable or dispersible buccal strip, a chewing gum, a tablet, a capsule, an emulsion, a suspension, an oral spray, effervescent, dissolvable granules or powder, a sachet, or a clear beverage.

The compositions disclosed herein may be used for replacing caffeine in foods, beverages, and other products. When caffeine is reduced or removed from coffee, colas, energy drinks, sports drinks, or foods, the resulting product loses the desirable CNS stimulant activity of caffeine. However, it also loses the harmful side effects of caffeine, including nausea, fast or irregular pulse, irritability, and loss of concentration. Removing all or part of the caffeine in a product with an extract of *Cyperus esculentus* peel and/or rhizomes, mangiferin or an extract comprising mangiferin, or a mixture thereof allows the side effects of caffeine to be removed, while restoring the desired CNS stimulant activity. Chufa extract in an amount of about 200 mg to about 20 grams, about 500 mg to about 15 grams, or about 1 gram to about 8 grams, may be used to replace all or part of the caffeine in a food, beverage or supplement. It is estimated that about 5 grams chufa extract is equivalent to 50 mg caffeine. Similarly, Mangiferin and mangiferin-containing extracts may be used to replace all or part of the caffeine in a food, beverage or supplement. It is estimated that about 100 to about 200 mg mangiferin is equivalent to 50 mg caffeine.

Accordingly, the current disclosure contemplates administration of a composition comprising:
  from about 25% to about 99.5% by weight, about 50% to about 99% by weight, about 70% to about 95% by weight, or about 80% to about 90% by weight, of mangiferin or an extract comprising mangiferin; and from about 0.5% to about 75% by weight, about 1% to about 50% by weight, about 5% to about 30% by weight, or about 10% to about 20% by weight of caffeine; or
  from about 25% to about 99.5% by weight, about 50% to about 99% by weight, about 70% to about 95% by weight, or about 80% to about 90% by weight, of a mixture of a) an extract of *Cyperus esculentus* peel and/or rhizomes, and b) and mangiferin or an extract comprising mangiferin; and c) from about 0.5% to about 75% by weight, about 1% to about 50% by weight, about 5% to about 30% by weight, or about 10% to about 20% by weight of caffeine;

A composition combining *Cyperus esculentus* extract and Mangiferin in a ratio of between about 20:1 and 1:1 may be used as to replace all or part of the caffeine in a caffeine-containing food, beverage, pharmaceutical, or neutraceutical. From about 20 mg to about 200 mg of the *Cyperus esculentus* extract/Mangiferin combination may be used to replace 1 mg of caffeine. The combined *Cyperus esculentus*-mangiferin or mangiferin containing plant extract is used in an amount of between 10 mg and 20 g for caffeine substitution or replacement.

The *Cyperus esculentus* extract/Mangiferin composition in accordance with the invention may be a simple mixture of the two ingredients after the extraction process. The invention may advantageously include additional ingredients with the purpose to further increase the energy boosting effect. Therefore it may be advantageous to add for example an energy-boosting component such as guarana, caffeine, theanine, theobromine, synephrine, ibogaine, yangonin, octopamine, and puerarin to the combined product presented, to enhance the energy-boosting effect provided by the present invention. The same products can also be added to *Cyperus esculentus* extract or Mangiferin separately.

To improve other aspects of the invention, as for example increasing the effect on mood and well-being, natural products like *Ganoderma*, Garcinia, Ginkgo, *Ginseng*, *Rhodiola* and *Astragalus* can be combined with the composition. Ingredients enhancing absorption and bioavailability may be added, like Piperin, Capsaicin, Aframomum or Ginger. Natural and artificial sweeteners, and flavors such as coffee, vanilla, hazelnut, chocolate, cream, or fruit flavor, can be integrated. Nutrients like omega-3 fatty acids, vitamins and minerals may be added. For athletes, adaptogens including Withania and *Rhodiola*, products improving muscle health and recovery like the amino acids citrulline and phosphatidylserine, natural nitrate sources including spinach and beetroot, anabolic or anti-catabolic components like ecdysterones and ursolic acid, and antioxidants may be added. Suitable antioxidants include polyphenols with anti-oxidant or xanthin-oxidase inhibitory effects can be added. Representative polyphenols include catechins from Green tea, polyphenols from Cocoa, Resveratrol from grape, *Polygonum* or *Gnetum gnemon* seeds, xanthohumol from *Humulus lupulus*, and luteolin, rutin or quercetin.

The *Cyperus esculentus* extract/Mangiferin composition may be combined with anti-inflammatories such as *Curcuma* and Ginger, and/or cognition improving-products such as Ginkgo, citicoline or huperzine. For people with problems of sexual performance, the *Cyperus esculentus* extract/Mangiferin composition may be combined with an aphrodisiac like icarine, yohimbine, luteolin or Kaempferia species.

The amount of the additional ingredient included in the in the composition of the present invention varies depending on the characteristics of each additional ingredient. The invention can, for example, be combined with an antioxidant in a ratio from 1:50 to 50:1.

The composition has a wide range of useful applications for the industry: it can be provided as a caffeine replacement or reducer in a liquid, syrup, or solid (tablet) or pulverized or granulated or gum form or can be incorporated into food products of liquid, solid (tablet), syrup granulated or pulverized consistency. The liquid may be presented in a concentrated form to be diluted by mixing it with teas, caffeine-free coffee, water or milk, juices, yoghurts or smoothies to provide the final consumable liquid low-caffeine or caffeine-free beverage providing the alertness, attention and concentration enhancing benefits typically associated with caffeine. The concentration of the present invention varies depending on the product format, purpose and/or the additional ingredients.

Example 1

Test Subjects:
Fisher 344 rats (11 months of age and day-night converted, weight about 350-400 g, provided by Charles River Laboratories, D-97633, Sulzfeld) were used in a series of experiments on the effects of various herbal and pharmaceutical products on central nervous system activity. Products were provided to the test subjects orally (gavage).
Test Substances:
The substances tested in this study included:
A control vehicle (0.9% NaCl);
Mangiferin, administered in an amount of 25 mg/kg to 6 rats;
*Cyperus esculentus* tuberous rhizome, ethanol extract, administered in an amount of 100 mg/kg to 7 rats;
Caffeine, administered in an amount of 1 mg/kg to 7 rats;
Guarana extract, a caffeine-containing botanical, administered in an amount of 15 mg/kg to 6 rats;
Citicolin, a nootropic with mental energy, attention and memory enhancing activities, administered in an amount of 48 mg/kg to 8 rats
*Cyperus esculentus* tuberous rhizome peel, ethanol extract, 150 mg/kg, plus Mango leaf extract, containing 60% of Mangiferin, 50 mg/kg, administered to 5 rats
Mango leaf extract, administered in an amount of 25 mg/kg to 8 rats EEG signals were recorded by telemetry from 4 implanted electrodes in the frontal cortex, hippocampus and striatum of freely moving rats from inside a totally copper shielded room. Signals were collected in sweeps of 4 second duration and Fast Fourier transformed using a Hanning window. EEG signals were recorded over a period starting 5 minutes after administration of the test substances, and ending 65 minutes after administration of the test substances. Sampling frequency was 512 Hz. Spectra were averaged in steps of 3 minutes each and displayed on-line. In an off-line procedure the spectra were averaged to give longer periods for further analysis and data presentation. Spectral activity within the frontal cortex, hippocampus, striatum and reticular formation was recorded. Oral administration of the control vehicle (0.9% NaCl) only resulted in very minor changes of spectral power within the four brain areas.

Through these in vivo animal encephalographic (EEG) studies, it has surprisingly been discovered that *Cyperus esculentus* tuberous rhizome extracts, mangiferin, mangiferin-containing botanical extracts and the combination of *Cyperus esculentus* tuberous rhizome peel extract and mangiferin are not only strikingly similar in CNS profile to each other, but also surprisingly similar to the CNS profiles of reference caffeine, citicolin and Guarana. As shown in FIG. 1, each of these extracts or compounds provides a decrease in spectral power in the in vivo EEG in the frontal cortex, hippocampus and striatum. Such decreases in this implanted brain electrode model correlate to an activation of underlying neurotransmission. As shown in FIG. 1, the effect of caffeine on the neural activity in the reticular formation is primarily directed to delta, alpha-2, and beta-1 waves ($p<0.01$, relative to pre-drug baseline), with less effect on the theta and alpha-1 waves ($p>0.1$). *Cyperus esculentus* tuberous rhizome extracts and mangiferin have an impact on delta, alpha-2, and beta-1 waves of the reticular formation which is similar to that of caffeine.

Administration of a mixture of *Cyperus esculentus* tuberous rhizome, 30% ethanol extract, and Mango leaf extract containing 60% Mangiferin decreased brain wave activity from delta, theta, alpha-1, alpha-2, beta-1, and beta-2 waves in the frontal cortex, the hippocampus, and the striatum to roughly the same extent as caffeine in an amount of 1 mg/kg, 15 mg/kg Guarana and 48 mg/kg Citicolin, as shown in FIG. 1

Example 2

Test Subjects:
Fisher 344 rats (11 months of age and day-night converted, weight about 350-400 g, provided by Charles River Laboratories, D-97633, Sulzfeld) were used in further experiments on the effects of *Cyperus esculentus* tuberous rhizome, ethanol extract, and mangiferin on central nervous system activity. Products were provided to the test subjects orally (gavage).
Test Substances:
The substances tested in this study included:
A control vehicle (0.9% NaCl);
*Cyperus esculentus* tuberous rhizome peel, 30% ethanol extract, administered in an amount of 200 mg/kg to 7 rats Mango leaf extract containing 60% Mangiferin, administered in an amount of 50 mg/kg to 6 rats; and a mixture of *Cyperus esculentus* tuberous rhizome peel, 30% ethanol extract, in an amount of 150 mg/kg, and Mango leaf extract containing 60% Mangiferin, in an amount of 50 mg/kg, the combination being administered to 6 rats.

EEG signals were recorded by telemetry from 4 implanted electrodes in the frontal cortex, hippocampus and striatum of freely moving rats from inside a totally copper shielded room. EEG signals were recorded over.

a first period, starting 5 minutes after administration of the test substances, and ending 65 minutes after administration of the test substances; and a second period, starting 245 minutes (4.1 hours) after administration of the test substances, and ending 305 minutes (5.1 hours) after administration of the test substances.

Gamma Waves in the Striatum:

Administration of a saline control had little impact on gamma wave activity in the striatum, as shown in FIG. 2A. *Cyperus esculentus* tuberous rhizome, 30% ethanol extract, likewise had little impact on gamma wave activity in the striatum, as shown in FIG. 2B. During the first period that the EEG was measured, ending 65 minutes after administration of the test substance, mango leaf extract containing 60% Mangiferin did not increase gamma wave activity in the striatum in a statistically significant manner, as shown in FIG. 2C. Between 4.1 and 5.1 hours after administration of the test substance there was no visible increase in gamma wave activity in the striatum, relative to the pre-drug baseline.

However, when *Cyperus esculentus* tuberous rhizome, 30% ethanol extract (100 mg/kg), and Mango leaf extract containing 60% Mangiferin (25 mg/kg) were combined, there was a very significant ($p<0.05$!) sizable and synergistic increase in gamma wave activity in the striatum. During the first period that the EEG was measured, ending 65 minutes after administration of the test substance, the *Cyperus esculentus* tuberous rhizome ethanol extract/Mango leaf extract combination synergistically increased gamma wave activity in the striatum for a period of at least 5.1 hours. During the first period that the EEG was measured, ending 65 minutes after administration of the test substance, the combination increased gamma wave activity in the striatum significantly ($p<0.05$), by about 80% relative to the pre-drug baseline, as shown in FIG. 2D. During the second period that the EEG was measured, ending 305 minutes after administration of the test substance, the combination increased gamma wave activity in the striatum significantly ($p<0.05$), by about 30% relative to the pre-drug baseline. Thus, the combination statistically significantly, and synergistically, increases both the level of gamma wave activity in the striatum, and the duration of the effect on gamma wave activity.

Motion:

Motion of the test subjects was recorded during recording of gamma wave activity in the striatum. The increase of gamma waves can indicate an increase of physical activity, an increase in alertness and attention, or both. The change in motion, measured in cm/hr, was recorded in subjects administered a saline control, and in subjects administered a combination of *Cyperus esculentus* tuberous rhizome, 30% ethanol extract (150 mg/kg), and Mango leaf extract containing 60% Mangiferin (50 mg/kg).

Motion in the presence of a mixture *Cyperus esculentus* peel extract 30% ethanol plus mango leaf extract (60% mangiferin) did not change compared to the vehicle, as shown in Table 1. During the 45 minute time period prior to administration of the test composition, rats administered the saline control and the chufa extract/mango leaf extract composition exhibited no significant difference in activity. Similarly, during a first time period beginning 5 minutes after administration of the saline control and the chufa extract/mango leaf extract composition, and ending 65 minutes after administration, as well as a second time period from about 4 to 5 hours after administration of the test compositions, there was no significant difference in activity between rats administered a saline control and rats administered the chufa extract/mango leaf extract composition. See Table 1. As no increase of physical motion has been demonstrated, this striatal gamma wave activity can be interpreted as an increase of alertness and attention.

TABLE 1

Effects of MIXTURE-TIGERNUT PEEL EXTRACT and MANGO LEAF EXTRACT on motion.

| | Motion [cm/h] | | | | |
|---|---|---|---|---|---|
| Time [min] | Vehicle 0.9% NaCl 1 ml/kg n = 8 | | *Cyperus esculentus* peel 150 mg/kg + Mango leaf (60% Mangiferin) 50 mg/kg n = 5 | | p |
| −45-0 | 690.02 | ±175 | 678 | ±180 | ns |
| 5-65 | 838.67 | ±55 | 845.49 | ±160 | ns |
| 245-305 | 555.48 | ±110 | 722.03 | ±155 | ns |

Changes in motion (cm/h) given for various time periods, relative to drug administration at 0 minutes. Mean average values are given ± S.E.M. Statistical comparison to the results with control (Vehicle) were determined using the Wilcoxon, Mann, Whitney U-test (p values are given on the right side, ns = not significant).

Neural Activity in the Frontal Cortex and Hippocampus:

Administration of a saline control had little impact on the neural activity in the frontal cortex and hippocampus, as shown in FIG. 2A. However, administration of *Cyperus esculentus* tuberous rhizome, 30% ethanol extract, significantly decreased brain wave activity in the frontal cortex. About an hour after administration of the *Cyperus esculentus* extract, brain wave activity in the frontal cortex from delta-, theta-, alpha-, and beta-waves decreased to, on average, about 60% of the pre-drug baseline, as shown in FIG. 2B. Simultaneously, delta and alpha-2 waves decreased significantly in the hippocampus ($p<0.1$). After about 5 hours, the effect on delta and alpha-2 waves in the hippocampus was no longer visible, although suppressed activity in the frontal cortex was still present.

Administration of Mango leaf extract containing 60% Mangiferin also decreased brain wave activity in the frontal cortex. About an hour after administration of the Mango leaf extract, brain wave activity in both the frontal cortex and the hippocampus from delta, theta, alpha-2, and beta-1 waves decreased noticeably, as shown in FIG. 2C. The decrease in delta and theta wave activity was statistically significant ($p<0.05$). After about 5 hours, there was no significant change in brain wave activity in the hippocampus or in delta and theta waves in the frontal cortex, relative to the pre-drug baseline, although suppressed activity in alpha and beta waves in the frontal cortex was present.

Administration of a mixture of *Cyperus esculentus* tuberous rhizome peel, 30% ethanol extract, and Mango leaf extract containing 60% Mangiferin decreased brain wave activity in the frontal cortex to roughly the same extent as *Cyperus esculentus* tuberous rhizome, 30% ethanol extract, alone. About an hour after administration of combined extracts, brain wave activity in the frontal cortex and the hippocampus from delta, theta, alpha-1, alpha-2, and beta-1 waves decreased significantly ($p<0.01$), as shown in FIG. 2D. Simultaneously, brain wave activity in the hippocampus from theta, alpha-1, and alpha-2 waves decreased significantly ($p<0.05$ for alpha-1 and alpha-2 waves; $p<0.1$ for theta waves). After about 5 hours, there was no significant change in brain wave activity from theta, alpha-1, alpha-2, beta-1, and beta-2 waves in the frontal cortex, relative to the pre-drug baseline, although suppression of brain wave activity in the hippocampus was present. In the hippocampus, suppression of activity from theta, alpha-1, alpha-2, beta-1, and beta-2 waves was observed ($p<0.05$ for alpha-1 waves; $p<0.1$ for theta, alpha-2, beta-1, and beta-2 waves). Additionally, relative to the saline control, the *Cyperus esculentus* alone, and the Mango leaf extract alone, the combination of the *Cyperus esculentus* and the Mango leaf extract produced a statistically significant ($p<0.05$) increase in gamma wave activity in the frontal cortex.

Synergism is observed in brain wave activity in the hippocampus upon administration of a mixture of *Cyperus esculentus* tuberous rhizome peel, 30% ethanol extract, and Mango leaf extract containing 60% Mangiferin. First, neither the *Cyperus esculentus* extract nor the Mango leaf extract has a statistically significant impact on alpha-1 brain wave activity in the hippocampus, either in the first hour after administration or 5 hours after administration, as shown in FIGS. 2B and 2C. However, the combination of *Cyperus esculentus* extract and the Mango leaf extract has a statistically significant impact on alpha-1 brain wave activity in the hippocampus, both in the first hour after administration and 5 hours after administration ($p<0.05$, both 1 hour after administration and 5 hours after administration). Further, neither the *Cyperus esculentus* extract nor the Mango leaf extract has any statistically significant impact on brain wave activity in the hippocampus 5 hours after administration, as shown in FIGS. 2B and 2C. The combination of *Cyperus esculentus* extract and the Mango leaf extract has a synergistic, statistically significant impact on alpha-brain wave activity in the hippocampus 5 hours after administration, related to an increase of serotonergic activity. Finally, only the combination of *Cyperus esculentus* extract and Mango leaf extract provides a statistically significant increase in gamma activity in the frontal cortex.

Example 3: Human Studies

Four Week Study

Four adults participated in a 4 week observational study, taking:
  3 grams of a 30% ethanol extract of *Cyperus esculentus* tuberous rhizome, one to two times daily for a week,
  400 mg of a mango leaf extract containing 284 mg of mangiferin, taken once daily for a week, and
  a combination of 3 grams of the *Cyperus esculentus* tuberous rhizome extract and 400 mg mango leaf extract, taken once to twice daily for two weeks.

The subjects made self-reported notes in diaries on side-effects, well-being, mood, concentration, alertness, stress. No side-effects were experienced. All of the subjects noted distinctly improved mood and well-being, and increased alertness, focus, and concentration that lasted from 3 to 5 hours after ingestion of the *Cyperus esculentus* tuberous rhizome extract, the mango leaf extract, and the combination of the mango leaf extract and Tigernut extract.

Two Week Study

In a 2-week observational study where 9 adults ingested a combination of 3 grams of the *Cyperus esculentus* tuberous rhizome extract and 400 mg mango leaf extract daily over a two week period, none of the side-effects that typically result from high caffeine intake were noted, such as nausea, fast or irregular pulse, irritability, loss of concentration, and jitters.

Addictive Potential

In a study where 6 adults ingested a combination of 3 grams of the *Cyperus esculentus* tuberous rhizome extract and 400 mg mango leaf extract daily over a two week period, no signs of addiction or withdrawal were observed. In a similar study where 2 adults ingested a combination of 3 grams of the *Cyperus esculentus* tuberous rhizome extract and 400 mg mango leaf extract daily over a two month period, no signs of addiction or withdrawal were observed. Further, daily intake over 2 months did not show any negative side-effects.

Two human subjects ingested larger doses of intake of the *Cyperus esculentus* tuberous rhizome/mango leaf extract in high doses (up to 20 g/day); increasing the dosage did not increase the observed effect on mood, alertness, focus, and concentration.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

Example 4: EEG Studies in Humans

A double blind, randomized study was done, whereby participants in a test group received a single dose of the combination product containing Ig chufa peel extract and 300 mg mangiferin in a *Mangifera indica* extract. Quantitative-topographical EEG combined with Eye-Tracking was recorded during different cognitive and emotional challenges. A second group (the placebo group) was administered a chufa- and mangiferin-free placebo. The result of this study demonstrated that the combination product, when compared to the placebo, induces changes in human electric brain activity, mainly in alpha2 waves, that can be correlated with enhanced cognitive processes.

Figure 3A:
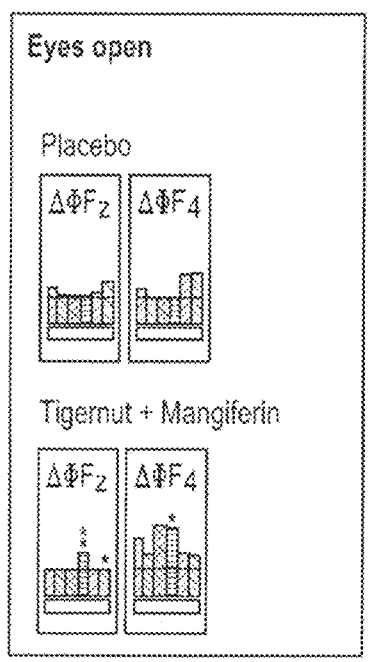
FIGS. 3A to 3C show the impact of a mixture of chufa peel extract and *Mangifera indica* extract on alpha waves in human subjects, using EEG data recorded under the recording conditions: "Eyes open" (FIG. 3A) the Stroop test (FIG. 3B) and fixation on a cross (FIG. 3C). Each graph in FIGS. 3A to 3C shows, from left to right, gamma, theta, alpha-1, alpha-2, beta-1, beta-2, and gamma waves.
Figure 3B:
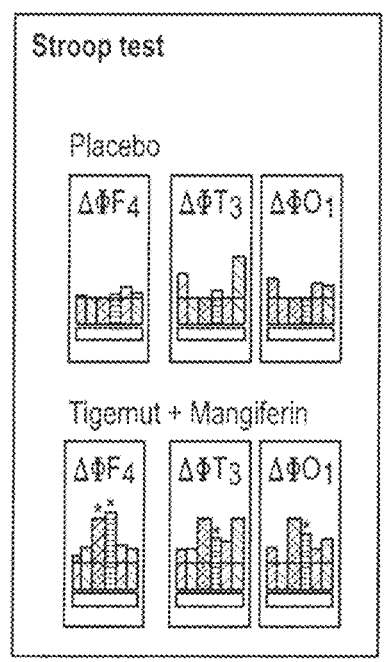
Figure 3C:
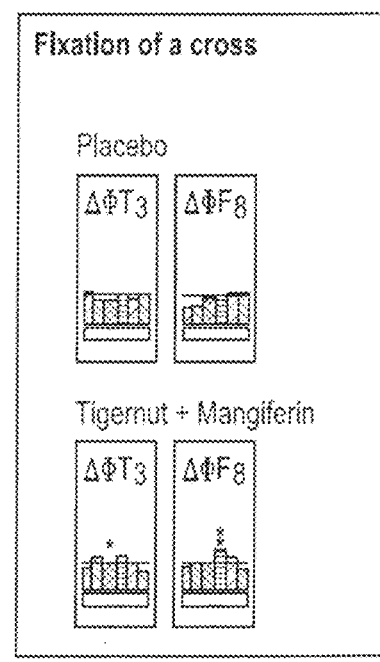

As an example, the EEG results for the recording condition "Eyes open", fixation of a cross, and the Stroop test for attention and concentration are reported (FIG. 3). A comparison of the EEG results for persons administered a combination of chufa peel extract and mangiferin was significantly different from EEG results for persons administered a placebo. The combination of chufa peel extract and mangiferin resulted in a statistically significant increase of alpha2 spectral power at electrode positions Fz and F4 under the recording condition "eyes open" for the test group, when compared to alpha2 spectral power at electrode positions Fz and F4 for the placebo group.

In the Stroop test, an increase of alpha2 waves was observed at frontal, temporal and occipital electrode positions F4, T3 and O1 in persons in the test group, relative to persons in the placebo group. The increase in alpha2 waves at electrode positions F4, T3 and O1 was statistically significant, when compared to corresponding values observed in the placebo group.

Under the recording condition "Fixation on a cross on the screen", which asks for some concentration, an increase of alpha1 and alpha2 waves was observed at electrode positions T3 and T8, in persons in the test group, relative to persons in the placebo group. The increase in alpha1 and alpha2 waves at positions T3 and T8 was statistically significant, when compared to corresponding values observed in the placebo group.

The elevated alpha waves are interpreted as enhanced attention and processing speed. Improvements were noted in the following psychometric tests group taking the chufa peel extract-mangiferin combination, in comparison to the results for a group taking a placebo: Picture comparison test, Stroop test, Processing Speed, Memory test, Brain Teaser test, and d2-test.

Example 5: EEG Studies in Rats Administered Mangiferin and/or Caffeine

The effect of mangiferin, caffeine, and mangiferin/caffeine mixtures on rat EEG signals was studied by recording activity of frontal cortex, hippocampus, striatum and reticular formation tissues of freely moving rats from inside a copper shielded room. After automatic artefact rejection, signals were collected in sweeps of 4 s duration and Fast Fourier transformed using a Hanning window. The resulting electrical power spectra were divided into 8 specially defined frequency ranges (delta: 1.50-4.00 Hz; theta: 4.25-6.75 Hz; alpha1: 7.00-9.50 Hz; alpha2: 9.75-12.25 Hz; beta1a: 12.50-15.00 Hz; beta1b: 15.25-17.75 Hz; beta2: 18.00-34.25 Hz; gamma: 34.50-81.00 Hz).

All dosages of caffeine and its combination with Zynamite® (mango leaf extract containing 60% mangiferin) were administered as solutions in an aqueous vehicle, where the solutions were prepared fresh for each experimental day and administered orally by gavage after 45 minutes of pre-drug Vehicle recording. Nine adult male Fisher 344 rats (5 months of age and day-night converted, weight about 350-400 g, were implanted with electrodes into the brain and were given two weeks for recovery from surgery. Three animals dropped the implant after performance of a placebo series. After testing two mangiferin/caffeine combinations, one further animal dropped the implant, so only five animals were tested on pure caffeine.

During the recording rats were not restricted and could move freely, but did not have food available to avoid artefacts. A crossover design with at least three days of drug holidays in between drug administrations was used. Animals were treated with oral administration of 1.0 ml/kg of vehicle (0.9% NaCl); mango leaf extract containing 60% mangiferin (25 mg/kg); caffeine (0.50 mg/kg); and mixtures of mango leaf extract containing 60% mangiferin (25 mg/kg) and caffeine (0.25 or 0.50 mg/kg). The animals were dosed orally at a constant volume of 1.0 ml/kg per kg body weight. The dosage administered to each animal was determined every day by the weight of that animal at the time of administration. Data were averaged from 5-9 animals, and are expressed as mean values±S.E.M.

Figure 4:
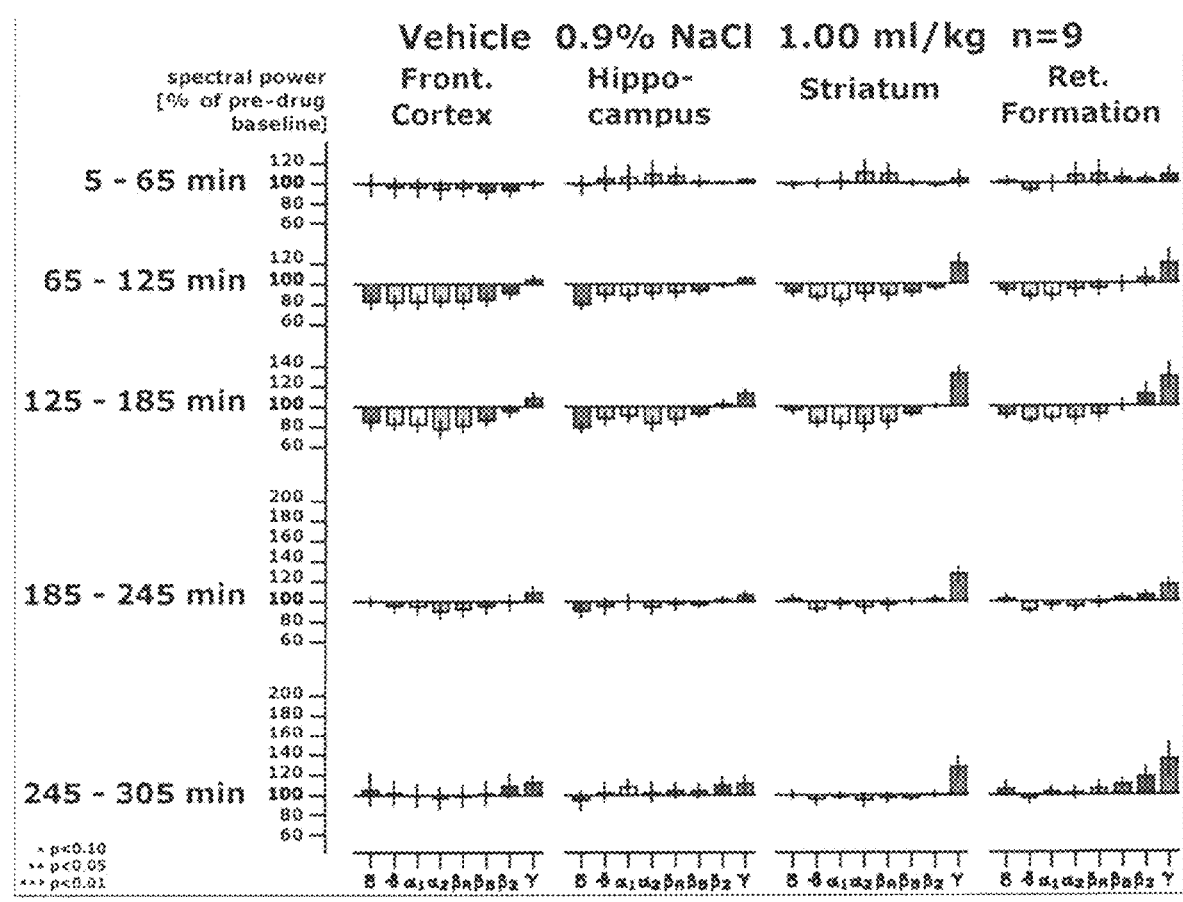
FIG. 4 shows EEG studies on a rat brain, showing the effect of a vehicle comprising 0.9% NaCl (1.0 ml/kg)

Rats were orally administered 1.0 ml/kg of vehicle (0.9% NaCl); mango leaf extract containing 60% mangiferin (25 mg/kg); caffeine (0.50 mg/kg); and mixtures of mango leaf extract containing 60% mangiferin (25 mg/kg) and caffeine (0.25 or 0.50 mg/kg). Oral administration of the vehicle (0.9% NaCl) resulted in small changes of spectral power within the frontal cortex, hippocampus, striatum and reticular formation. As seen in FIG. 4, during the second to the fifth hours, minor decreases of power (typically less than 20% of the pre-drug baseline) emerged in the frontal cortex and hippocampus. With respect to gamma power, increases of 20% to 40%, relative to the pre-drug baseline, were observed in the striatum and reticular formation.

Figure 5:
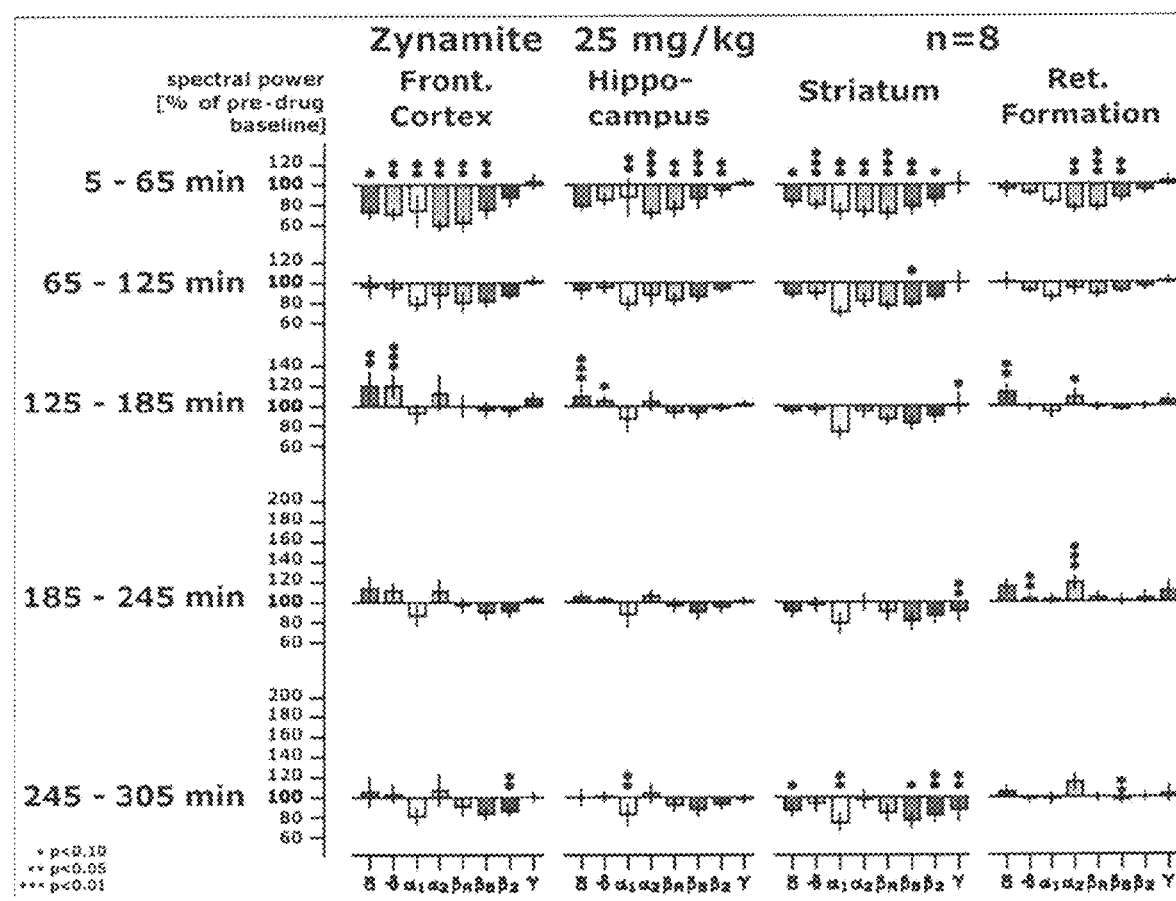
FIG. 5 shows EEG studies on a rat brain, showing the effect of a mango leaf extract, containing 60% by weight mangiferin (25 mg/kg)

As seen in FIG. 5, oral administration of 25 mg/kg of mango leaf extract comprising 60% mangiferin (Zynamite®) resulted in a statistically significant attenuation of all classic frequencies during the first hour after administration. The strongest effects were observed in the alpha2 and beta1 spectral frequencies. Within the frontal cortex and striatum, the theta; alpha1; alpha2; beta1a; and beta1b spectral power was reduced by about 25% to about 45% during the first hour after administration, relative to the pre-drug baseline. When compared to the changes in EEG observed after administration of the vehicle alone, these reductions were statistically significant ($p<0.05$). During the third hour after administration significant increases of delta power were seen in the frontal cortex, hippocampus, and reticular formation ($p<0.05$).

Figure 6:
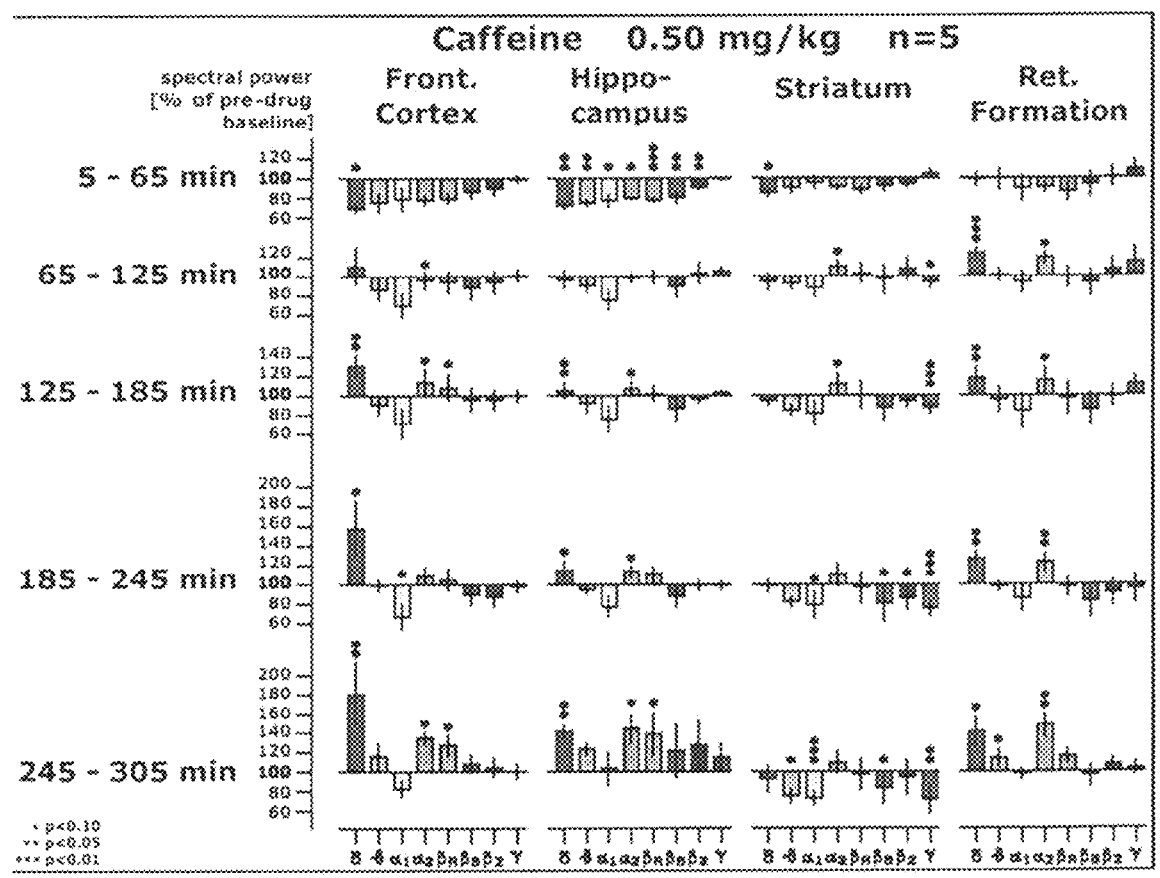
FIG. 6 shows EEG studies on a rat brain, showing the effect of caffeine (0.5 mg/kg)

As seen in FIG. 6, oral administration of Caffeine (0.50 mg/kg) resulted in a statistically conspicuous attenuation ($p<0.1$) of delta power in the frontal cortex. In the hippocampus statistically significant attenuation of delta, theta and beta power was recognized. In the striatum a minor but statistically conspicuous decrease of delta waves was seen. From the second hour after administration on, statistically significant increases of delta power emerged for the rest of the recording period in the frontal cortex and reticular formation. During the last hour increases of alpha2 power were observed except for the striatum; the increase in alpha2 power is particularly significant ($p<0.05$) in the reticular formation.

Figure 7:
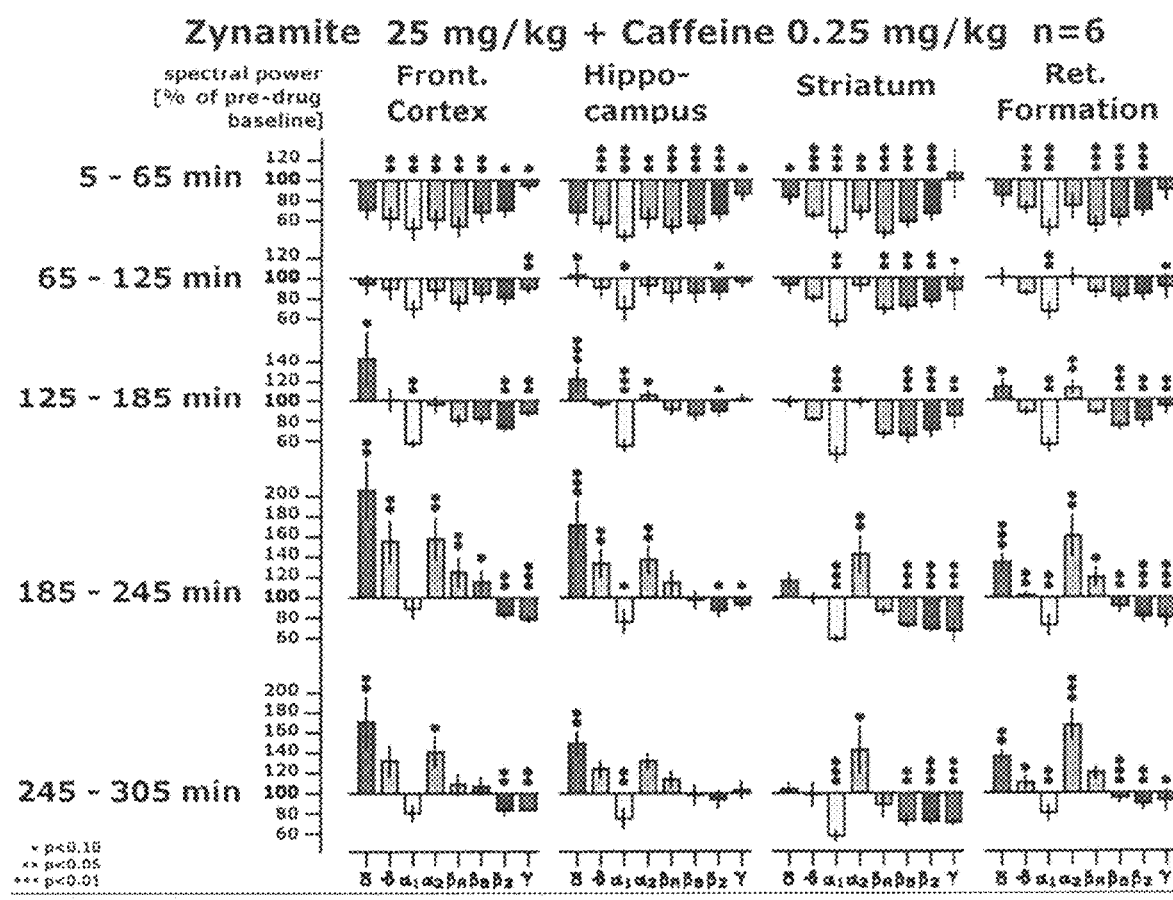
FIG. 7 shows EEG studies on a rat brain, showing the effect of a combination of mango leaf extract, containing 60% by weight mangiferin (25 mg/kg); and caffeine (0.25 mg/kg)

As seen in FIG. 7, oral administration of the combination of mango leaf extract (25 mg/kg) and Caffeine (low dose: 0.25 mg/kg) resulted in a statistically significant attenuation of all frequencies except for delta and gamma spectral power in all brain regions during the first hour after administration, in comparison to the vehicle. The strongest attenuation was seen in alpha1 and beta1 power. The alpha1 attenuation lasted into the third hour after administration in the frontal cortex, hippocampus, and reticular formation, and into the fifth hour within the striatum. During the third hour an increase of delta power emerged in the frontal cortex, hippocampus, and reticular formation. At the same time, significant increases of alpha2 power were documented during the last fourth and fifth hours after administration.

Figure 8:
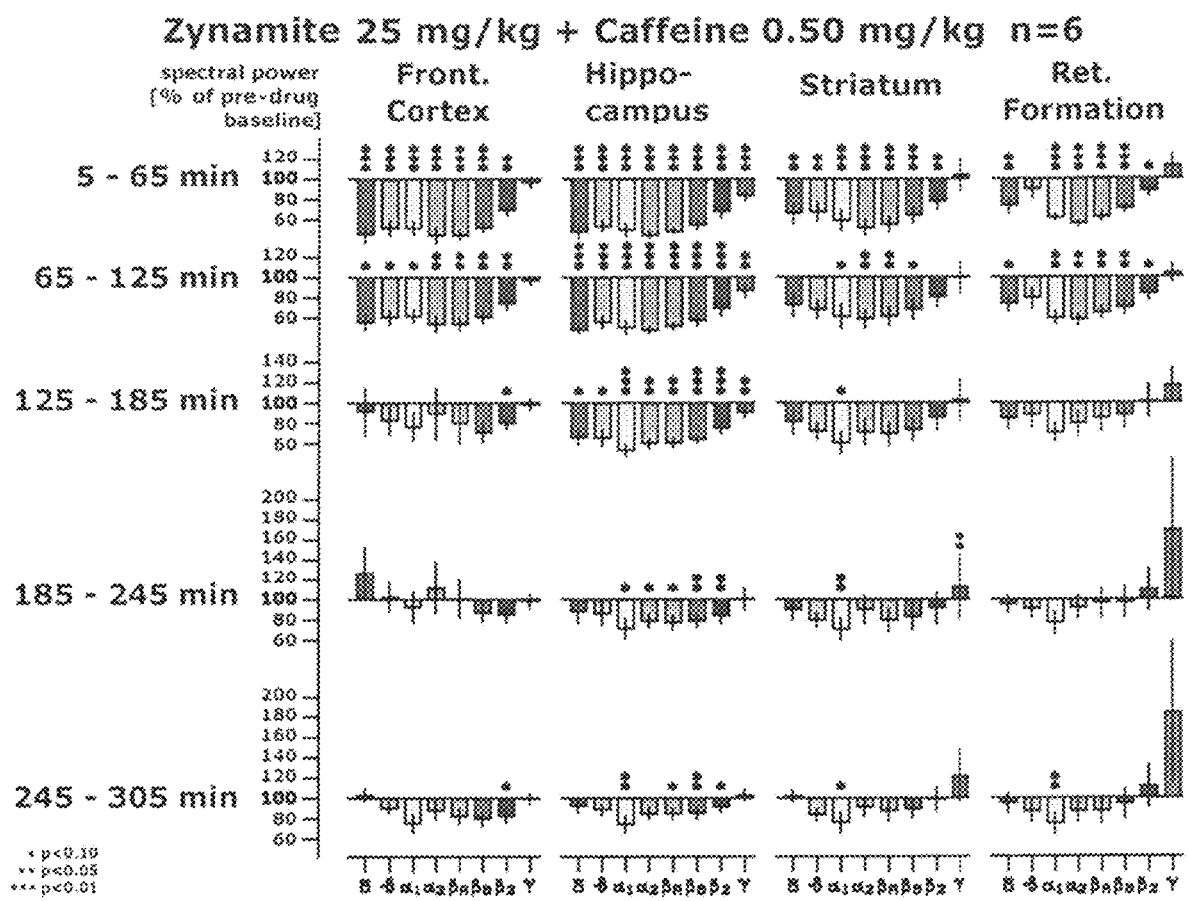
FIG. 8 shows EEG studies on a rat brain, showing the effect of a combination of mango leaf extract, containing 60% by weight mangiferin (25 mg/kg); and caffeine (0.50 mg/kg)

As seen in FIG. 8, oral administration of the combination of mango leaf extract (25 mg/kg) and Caffeine (high dose: 0.50 mg/kg) resulted in a statistically significant attenuation of all frequencies except for gamma spectral power in all brain regions during the first hour after administration, in comparison to the vehicle. The effects were strongest in frontal cortex and hippocampus ($p<0.01$ for delta, theta, alpha1, alpha2, beta1a, beta1b, and beta2 power). The statistically significant attenuation lasted until the second hour after administration in the frontal cortex and, striatum, and reticular formation. In the hippocampus, statistically significant attenuation of alpha2 waves lasted into the fourth hour after administration, and statistically significant attenuation of alpha1 and beta waves lasted into the fifth hour.

As seen in FIG. 7, the combination of mango leaf extract and a low dose of caffeine shows a strong attenuation of alpha1 waves in all brain regions, which is long-lasting and statistically significant relative to the vehicle (in the third hour after administration, $p<0.05$ for alpha1 attenuation in the frontal cortex and reticular formation, and $p<0.01$ for alpha1 attenuation in the hippocampus and striatum). A large attenuation of all frequencies is observed in the presence of the combination of mango leaf extract with a higher dose of caffeine, as seen in FIG. 8. Interestingly, in the third to fifth hours after administration of mango leaf extract and a low dose of caffeine, statistically significant increases in delta and alpha2 power are observed, as shown in FIG. 7. However, in the third to fifth hours after administration of mango leaf extract and a high dose of caffeine, no significant increases in delta and alpha2 power are seen, as shown in FIG. 8.

Figure 9:
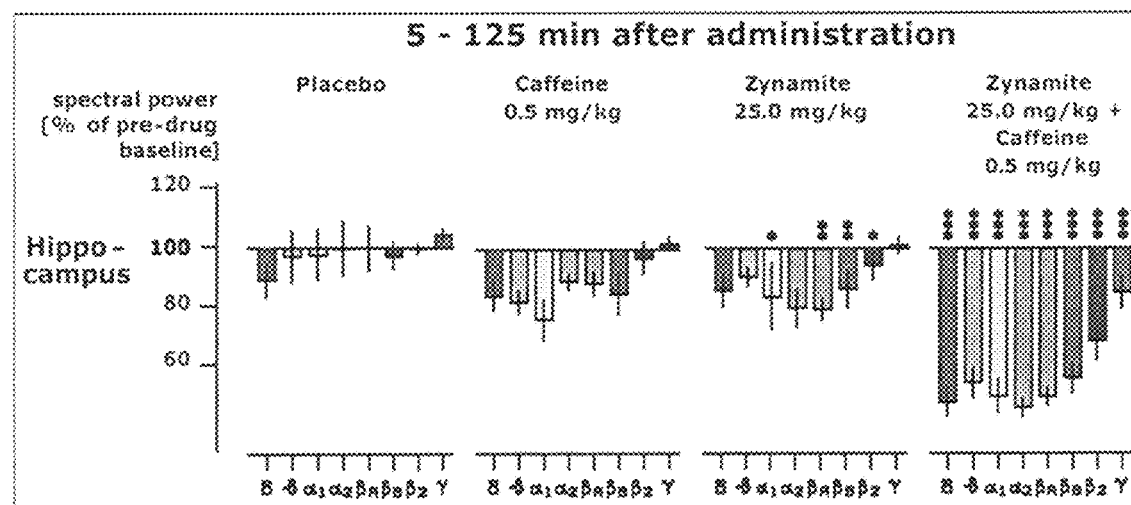
FIG. 9 shows a direct comparison of EEG changes observed in the presence of mango leaf extract, containing 60% by weight mangiferin, and caffeine, alone and in combination, during the first two hours after administration.

The large attenuation of brain wave frequencies in the presence of the combination of mango leaf extract with caffeine indicates a synergistic action, which is clearly demonstrated when looking at the frequency changes in the hippocampus during the first 2 hours after administration mango leaf extract and a high dose of caffeine, as shown in FIG. 9.

Example 6: Ex Vivo Analysis of Population Spikes in the Hippocampal Slice Preparation Hippocampus slices of rat brains were tested. After daily administration of trial medication for one week, 4 animals were sacrificed under deep anesthesia and the hippocampus was removed and chopped by a vibrating razor blade to give 6 slices of about 400 t thickness per animal. Slices were taken one day after the last treatment. After adaptation to artificial cerebrospinal fluid for one hour, slices were transferred to an incubation chamber and superfused with cerebrospinal fluid at 35° C.

Schaffer collaterals are branches extending from the axons of CA3 pyramidal cells in the hippocampus. Schaffer collaterals project to the CA1 area of the hippocampus, and are an integral part of memory formation. The Schaffer Collaterals were stimulated by single stimuli or theta burst stimuli, where theta burst stimuli are short bursts of stimulation at high frequencies, applied 5 times per second. Stimulation resulted in the induction of a population spike in pyramidal cells. Amplitudes of the population spikes were recorded after stimulation every 10 minutes to prevent physiological potentiation mechanisms. Excitability of the hippocampus slices was checked after administration of 25 mg/kg of mango leaf extract containing 60% mangiferin; a combination of 25 mg/kg of mango leaf extract and 0.5 mg/kg of caffeine; and 0.5 mg/kg of caffeine alone.

Figure 10:
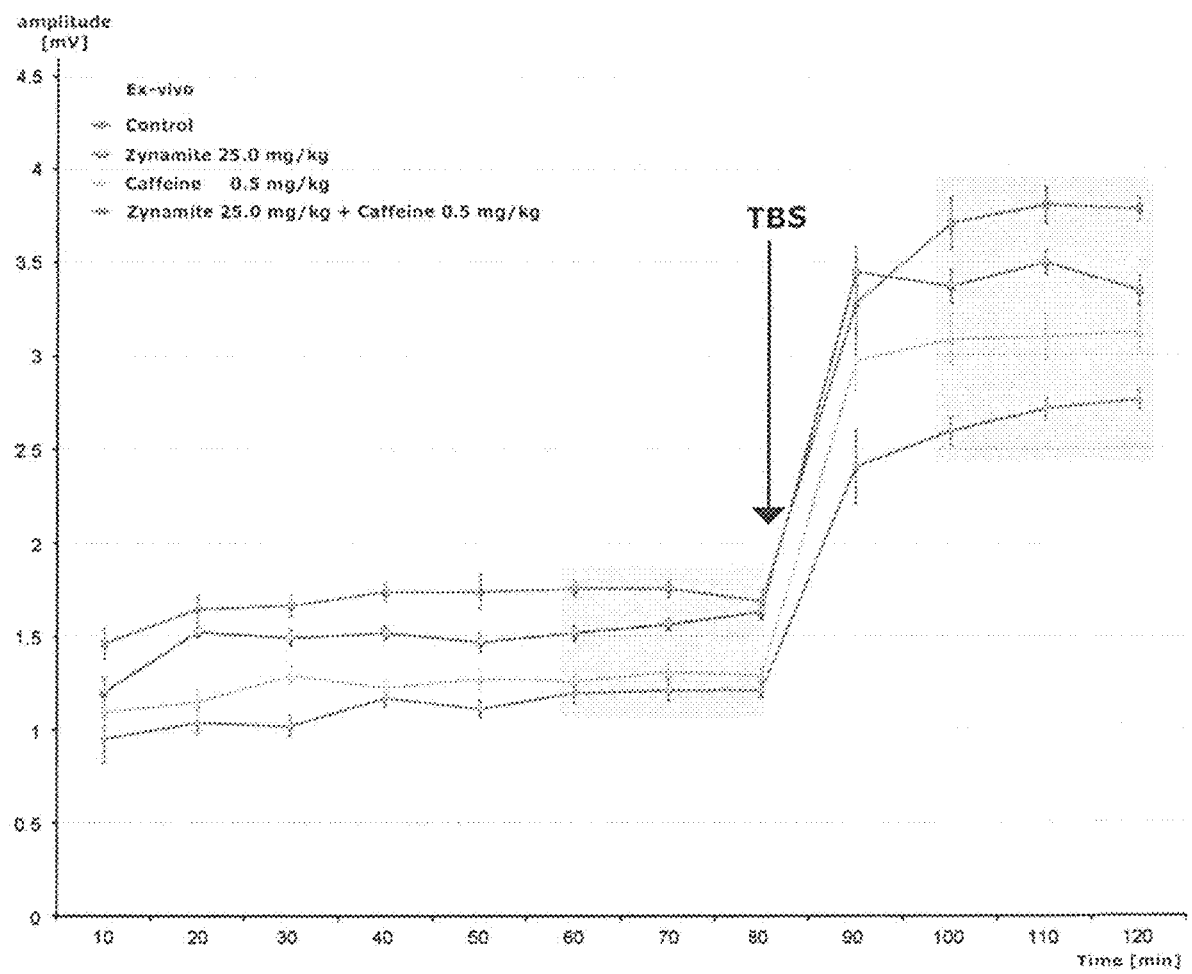
FIG. 10 shows the time dependent effects of placebo, caffeine (0.5 mg/kg), mango leaf extract (25.0 mg/kg), and a combination of both mango leaf extract (25.0 mg/kg) and caffeine (0.5 mg/kg) on pyramidal cell activity in hippocampal slices. Activity is measured in terms of changes of population spike amplitudes (as voltage on the ordinate). Results were obtained after performance of single stimuli (10-80 min) or after theta burst stimuli (90-120 min)

FIG. 10 shows the time dependent effects of placebo, caffeine (0.5 mg/kg), mango leaf extract (25.0 mg/kg), and a combination of both mango leaf extract (25.0 mg/kg) and caffeine (0.5 mg/kg) on pyramidal cell activity in hippocampal slices. Activity is measured in terms of changes of voltage change following stimulation, which correlates to a pyramidal cell population spike. Results were obtained after performance of single stimuli at 10-minute intervals (10-80 min after initial stimulation). Eighty minutes after the initial stimulation with a single stimulus, the first theta burst stimulus was applied. Theta burst stimuli were repeated every 10 minutes (90-120 min after initial stimulation), as shown in FIG. 10. As seen in FIG. 10 (time t=60-80 min.), application of single stimuli to a hippocampal slice from a rat treated with high dose caffeine leads to a small increase in voltage following stimulation, relative to the control slices from rats administered placebo. Application of single stimuli to a hippocampal slice from a rat treated with mango leaf extract or a mixture of mango leaf extract and high dose caffeine leads to a large increase in voltage, relative to control slices. Application of theta burst stimuli to a hippocampal slice from a rat treated with mango leaf extract, caffeine, or a mixture of mango leaf extract and high dose caffeine leads to a significant increase in voltage, relative to control slices, as shown in FIG. 10 (time t=100-120 min.).

Figure 11:
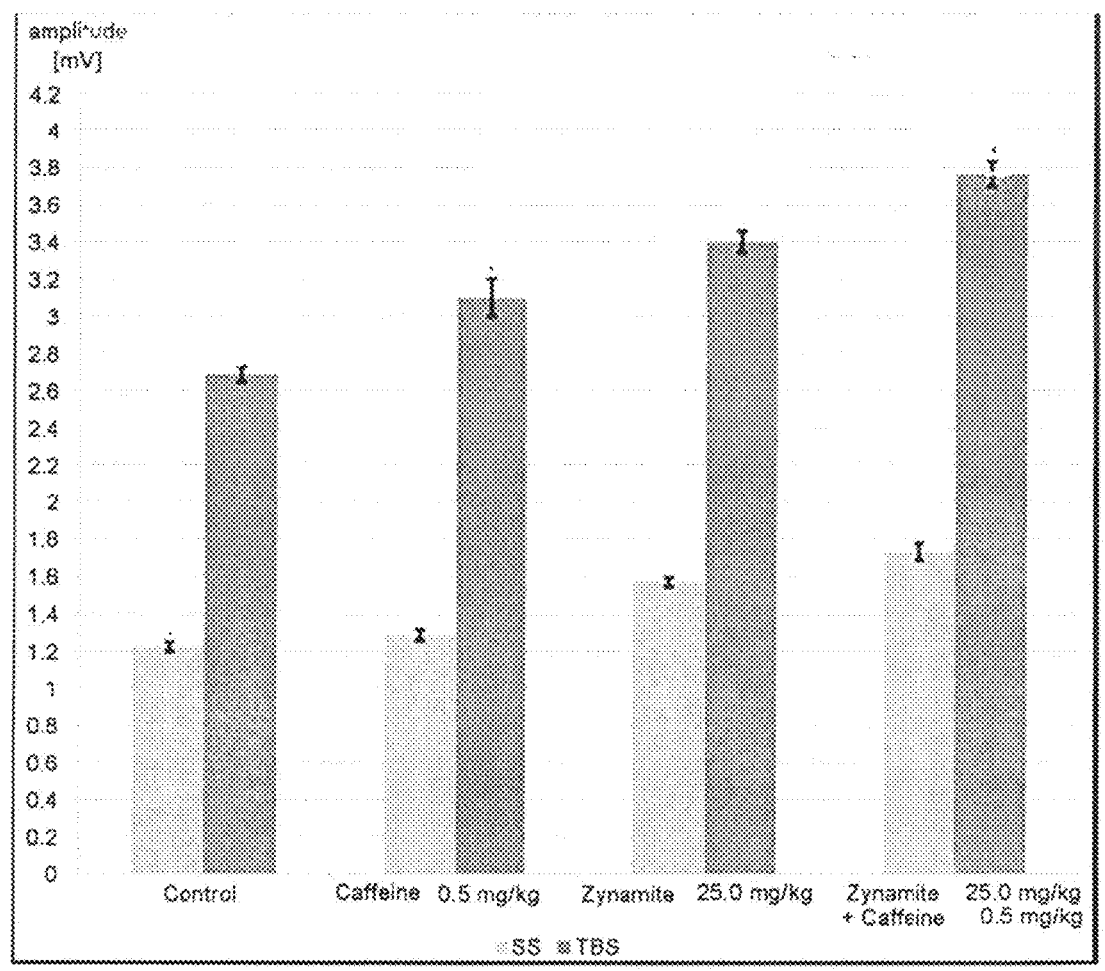
FIG. 11 shows the effects of a placebo, caffeine (0.5 mg/kg), mango leaf extract containing 60% by weight mangiferin (25.0 mg/kg), and a combination of both (mango leaf extract, 25.0 mg/kg, and Caffeine, 0.5 mg/kg) on pyramidal cell activity in terms of changes of population spike amplitudes (as voltage on the ordinate).

FIG. 11 shows the effects of a placebo), caffeine (0.5 mg/kg), mango leaf extract containing 60% by weight mangiferin (25.0 mg/kg), and a combination of both (mango leaf extract, 25.0 mg/kg, and Caffeine, 0.5 mg/kg) on pyramidal cell activity in terms of changes of population spike amplitudes (as voltage on the ordinate). The mean average values of three measurements (shadowed area in FIG. 10) are documented in FIG. 12; these values are reported with statistical significance in Table 1.

As seen in Table 1, pyramidal cell population spike amplitudes in hippocampal slices from rats administered high dose caffeine, where the slices are treated with single stimuli at 10-minute intervals, are not significantly different from population spike amplitudes in hippocampal slices from rats administered a placebo. Population spike amplitudes in hippocampal slices from rats administered high dose caffeine, where the slices are treated with theta burst stimuli at 10-minute intervals, are moderately higher than population spike amplitudes in hippocampal slices from rats administered a placebo; this difference is statistically significant ($p<0.05$).

Population spike amplitudes in hippocampal slices from rats administered mango leaf extract, alone or in combination with high dose caffeine, are higher than population spike amplitudes in hippocampal slices from rats administered either a placebo or caffeine in the absence of mango leaf extract. This difference is statistically significant, regardless of whether single stimuli or theta burst stimuli are used, as seen in Table 1.

TABLE 1

| Compound | Amplitude (mv) | Significance relative to placebo | Significance relative to caffeine |
| --- | --- | --- | --- |
| Placebo | 1.25 (SS)[1] | — | n.s. |
| | 2.7 (TBS)[2] | — | $p < 0.05$ |
| Caffeine (0.5 mg/kg) | 1.3 (SS) | n.s.[3] | — |
| | 3.1 (TBS) | $p < 0.05$ | — |
| Mango leaf extract (60% mangiferin, 25 mg/kg) | 1.55 (SS) | $p < 0.01$ | $p < 0.05$ |
| | 3.4 (TBS) | $p < 0.01$ | $p < 0.01$ |
| Mango leaf extract, 60% mangiferin/ Caffeine | 1.75 (SS) | $p < 0.01$ | $p < 0.01$ |
| | 3.75 (TBS) | $p < 0.01$ | $p < 0.01$ |

[1]SS = Single Stimulation.
[2]TBS = Theta Burst Stimulation.
[3]n.s. = not significant.

Thus, as seen in Table 1 and in FIG. 11, mango leaf extract, whether alone or in combination with caffeine, lead to increases in pyramidal cell populations and pyramidal cell activity. As pyramidal neurons in the prefrontal cortex are implicated in cognitive ability, and play a critical role in complex object recognition within the visual processing areas of the cortex, mano leaf extract may therefore increase cognitive function in the brain. While caffeine also appears to stimulate pyramidal cell activity to a moderate degree, as seen in FIG. 11, it has a significantly smaller effect on such activity than mango leaf extract.

Although various embodiments have been described in detail with particular reference to certain aspects thereof, it should be understood that the subject matter disclosed herein is capable of other embodiments, and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

What is claimed is:

1. A method for enhancing sports performance in a person in need thereof, comprising administering to said person:
   a) an effective amount of mangiferin, or norathyriol, or of a botanical extract comprising mangiferin or norathyriol; and
   b) an effective amount of caffeine,
   wherein:
      said effective amount of said mangiferin or said norathyriol is between 15 mg and 20 g per dose; or
      said effective amount of said botanical extract comprising mangiferin or norathyriol is sufficient to provide between 15 mg and 20 g mangiferin or norathyriol per dose.

2. The method according to claim 1, wherein said administering comprises administering a single composition comprising an effective amount of mangiferin or an extract comprising mangiferin; and an effective amount of caffeine.

3. The method according to claim 1, wherein said administering comprises administering a first composition comprising an effective amount of mangiferin or an botanical extract comprising mangiferin; and a second composition comprising an effective amount of caffeine.

4. A method for enhancing sports performance in a person in need thereof, comprising administering to said person:
   a) an effective amount of mangiferin, norathyriol, or a botanical extract comprising mangiferin or norathyriol; and
   b) an effective amount of caffeine,
      wherein said administering further comprises administering an extract of *Cyperus esculentus* peel, *Cyperus esculentus* rhizomes, or a combination thereof.

5. The method according to claim 2, wherein said single composition further comprises an extract of *Cyperus esculentus* peel, *Cyperus esculentus* rhizomes, or a combination thereof.

6. The method according to claim 3, wherein:
   said first composition further comprises an extract of *Cyperus esculentus* peel, *Cyperus esculentus* rhizomes, or a combination thereof;
   said second composition further comprises an extract of *Cyperus esculentus* peel, *Cyperus esculentus* rhizomes, or a combination thereof; or
   said administering further comprises administering a third composition comprising an extract of *Cyperus esculentus* peel, *Cyperus esculentus* rhizomes, or a combination thereof.

7. A method for enhancing sports performance in a person in need thereof, comprising administering to said person:
   a) an effective amount of mangiferin, norathyriol, or a botanical extract comprising mangiferin or norathyriol;
   b) an effective amount of caffeine; and
   c) a hydroalcoholic extract of peel of *Cyperus esculentus* rhizomes.

8. The method according to claim 1, wherein:
   the botanical extract comprising mangiferin or norathyriol comprises a defined content of mangiferin or norathyriol.

9. The method according to claim 8, wherein the botanical extract comprising mangiferin or norathyriol comprises the defined content of mangiferin or norathyriol, the defined content of mangiferin or norathyriol being between 10% and 99% by weight of the extract.

10. The method according to claim 8, wherein the botanical extract comprising mangiferin or norathyriol comprises the defined content of mangiferin or norathyriol, the defined content of mangiferin or norathyriol being about 60% by weight of the extract.

11. The method according to claim 1, wherein said botanical extract comprising mangiferin or norathyriol is a mangiferin-containing extract of a plant species in a genus selected from the group consisting of *Mangifera, Salacia, Cyclopia, Hypericum, Canscora, Fagraea, Gentiana, Hoppea, Swertia, Hypericum, Polygala, Zizyphus*, and mixtures thereof.

12. The method according to claim 1, wherein the ratio of a) to b) is between about 20:1 and about 200:1.

13. The method according to claim 12, wherein the ratio of a) to b) is between about 40:1 and about 150:1.

14. The method according to claim 13, wherein the ratio of a) to b) is between about 50:1 and about 100:1.

15. The method according to claim 1, wherein said effective amount of said caffeine is between 0.1 mg and 1 g per dose.

16. The method according to claim 1, wherein said composition further comprises an active ingredient selected from the group consisting of: B group vitamins, citicoline, citrulline, choline, curcumin, huperzine, luteolin, ursolic acid, ibogaine, magnesium, N-methyltyramine, oleamide, omega-3 fatty acids, octopamine, phosphatidylserine, quercetin, rutin, resveratrol, synephrine, taurine, taxifoline, theanine, theobromine, xanthohumol, yangonin, yohimbine, ecdysteroids (20HE) extracts of plant species of the genera *Aframomum, Aloysia, Alpinia, Astragalus, Bacopa, Centella, Citrus, Coca, Cola, Curcuma, Coffea, Celastrus, Camellia, Eleutherococcus, Ephedra, Euterpe, Garcinia, Ginkgo, Ganoderma, Glycyrrhiza, Icarine, Ilex, Irvingia, Kaempferia, Ocimum, Paullinia, Panax, Pfaffia, Piper Puerraria, Rhodiola, Rhaponticum, Sida, Sideritis, Tabernanthe, Theobroma, Vitis, Withania, Zingiber, Zizyphus*, and mixtures thereof.

17. The method according to claim 1, wherein said administration further comprises the administration of an active ingredient selected from the group consisting of luteolin, quercetin, rutin, *Rhodiola, Coffea* and mixtures thereof.

18. The method according to claim 1, wherein said method for enhancing sports performance is for enhancing reaction time, endurance, athletic performance, muscle health and/or recovery.

19. The method according to claim 1, wherein said method is for enhancing sports performance in training and endurance.

* * * * *